(12) United States Patent
Khan et al.

(10) Patent No.: US 11,766,435 B2
(45) Date of Patent: Sep. 26, 2023

(54) N3-SUBSTITUTED IMINOPYRIMIDINONES AS ANTIMALARIAL AGENTS

(71) Applicants: Merck Sharp & Dohme LLC, Rahway, NJ (US); The Walter and Eliza Hall Institute of Medical Research, Victoria (AU)

(72) Inventors: Tanweer A. Khan, Bridgewater, NJ (US); Jared N. Cumming, Winchester, MA (US); David B. Olsen, Lansdale, PA (US); Justin A. Boddey, Yarraville (AU); Alan F. Cowman, Melbourne (AU); Brad E. Sleebs, Victoria (AU)

(73) Assignees: Merck Sharp & Dohme LLC, Rahway, NJ (US); The Walter and Eliza Hall Institute of Medical Research, Victoria (AU)

( * ) Notice: Subject to any disclaimer, the term of this patent is extended or adjusted under 35 U.S.C. 154(b) by 830 days.

(21) Appl. No.: 16/076,400

(22) PCT Filed: Feb. 13, 2017

(86) PCT No.: PCT/US2017/017603
§ 371 (c)(1),
(2) Date: Aug. 8, 2018

(87) PCT Pub. No.: WO2017/142825
PCT Pub. Date: Aug. 24, 2017

(65) Prior Publication Data
US 2020/0230140 A1 Jul. 23, 2020

Related U.S. Application Data

(60) Provisional application No. 62/296,823, filed on Feb. 18, 2016.

(51) Int. Cl.
| | | |
|---|---|---|
| *A61K 31/4709* | (2006.01) | |
| *A61K 9/06* | (2006.01) | |
| *A61K 47/10* | (2017.01) | |
| *A61K 47/12* | (2006.01) | |
| *A61P 17/10* | (2006.01) | |
| *A61P 17/00* | (2006.01) | |
| *A61P 17/04* | (2006.01) | |
| *A61P 31/04* | (2006.01) | |
| *A61K 31/513* | (2006.01) | |
| *A61P 33/06* | (2006.01) | |
| *A61K 31/527* | (2006.01) | |
| *A61K 9/00* | (2006.01) | |
| *A61K 45/06* | (2006.01) | |

(52) U.S. Cl.
CPC .......... *A61K 31/513* (2013.01); *A61K 31/527* (2013.01); *A61P 33/06* (2018.01); *A61K 9/0019* (2013.01); *A61K 9/0053* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,579,353 B2 | 8/2009 | Fiandor Roman et al. | |
| 8,133,989 B2 * | 3/2012 | Rabbani | C12Q 1/6844 536/24.3 |

FOREIGN PATENT DOCUMENTS

| | | |
|---|---|---|
| WO | 2006138192 A1 | 12/2006 |
| WO | 2006138195 A1 | 12/2006 |
| WO | 2007146225 A2 | 12/2007 |
| WO | 2008103351 A2 | 8/2008 |
| WO | 2013142396 A1 | 9/2013 |
| WO | 2014160775 A1 | 10/2014 |

OTHER PUBLICATIONS

Zhu et al. (Discovery of Cyclic Acylguanidines as Highly Potent and Selective β-Site Amyloid Cleaving Enzyme (BACE) Inhibitors: Part I—Inhibitor Design and Validation. J. Med. Chem. 2010, 53, 951-965, DOI: 10.1021/jm901408p ) (Year: 2010).*
Caldwell, John P., et. al., Novel heterocycles as renin inhibitors, 244th ACS National Meeting & Exposition, 2012, MEDI-125.
Gambini, Luca, et al., Picomolar Inhibiton of Plasmepsin V, an Essential Malaria Protease, Achieved Exploiting the Prime Region, PLOS One, 2015, p. 1-35, vol. 10, No. 11.
Gamo, F. J. et al., Thousands of chemical starting points for antimalarial lead identification, Nature, 2010, p. 305-312, vol. 20.
McKittrick, Brian, A. et al., Iminopyrimidinones: A novel pharmacophore for the development of orally active renin inhibitors, Bioorganic & Medicinal Chemistry Letters, 2015, p. 1592-1596, vol. 25.
Vaccaro, Henry A. et al., Iminotetrahydropyrimidinones as renin inhibitors: A foray into the S3sp of renin, 244th ACS National Meeting & Exposition, 2012, MEDI-124.

* cited by examiner

*Primary Examiner* — Layla Soroush
(74) *Attorney, Agent, or Firm* — Sylvia A. Ayler; Catherine D. Fitch

(57) ABSTRACT

The present invention provides methods of treating malaria comprising administration of an N3-substituted iminopyrimidinone of Formula (I) or a pharmaceutically acceptable salt thereof, to a subject in need thereof, wherein the variables $R^1$, $R^2$, $R^3$, $R^4$, $R^5$, A, B, L, m, and n are as defined herein. The invention also provides uses of the compounds of Formula (I), as defined herein, for inhibiting plasmepsin V activity, for treating a *Plasmodium* infection, and for treating malaria. Also provided are methods of treatment further comprising administration of one or more additional anti-malarial compounds.

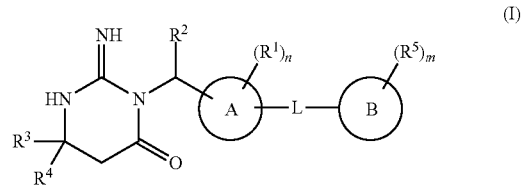

(I)

6 Claims, No Drawings

N3-SUBSTITUTED IMINOPYRIMIDINONES AS ANTIMALARIAL AGENTS

CROSS-REFERENCE TO RELATED APPLICATIONS

This application is a U.S. National Phase application under 35 U.S.C. § 371 of PCT Application No. PCT/US2017/017603, filed Feb. 13, 2017, which published as WO2017/142825 A1 on Aug. 24, 2017, and claims priority under 35 U.S.C. § 365(b) from U.S. provisional patent application No. 62/296,823, filed Feb. 18, 2016.

FIELD OF THE INVENTION

The present invention relates to methods of use of compounds of Formula (I) or a pharmaceutically acceptable salt thereof for the treatment of *Plasmodium* infections, more particularly to the treatment of malaria.

BACKGROUND OF THE INVENTION

Malaria is caused by the protozoan parasite *Plasmodium*, which is transmitted to humans via the bite of an infected *Anopheles* mosquito. Four species of malaria parasites can infect humans under natural conditions: *Plasmodium (P.) falciparum, P. vivax, P. ovale*, and *P. malariae*. While the first two species are responsible for the largest portion of the malaria burden, *P. falciparum* is often associated with severe, life-threatening symptoms (Richie and Saul, *Nature* 415:694-701 (2002)).

People suffering from malaria can exhibit a range of symptoms from fever, vomiting, headache and fatigue to more severe symptoms including seizures, coma, or even death if left untreated. Despite the availability of antimalarial drugs, malaria is still one of the world's most devastating diseases, causing approximately 438,000 deaths in 2015 alone. See World Health Organization, *WHO Global Malaria Programme, World Malaria Report* 2015. Geneva, Switzerland: WHO Press 2015. Those at highest risk for disease include children, pregnant women, and non-immune travelers from malaria-free areas. The burden of disease is disproportionately high in Sub-Saharan Africa, with 88% of new malaria cases and about 90% of malaria deaths, mostly children <5 years of age in 2015. *World Malaria Report, supra*.

Although there are drugs available for the treatment of malaria, the emergence of drug resistant strains of *Plasmodium* has caused many antimalarial drugs to lose their effectiveness in many areas of the world. Therefore, there is a continued need to discover and develop antimalarial agents that are effective against new and old strains of *Plasmodium*.

Aspartyl proteases are viewed as prime antimalarial targets, but the design of therapeutics to target them has been complicated by a lack of understanding on their essential roles in parasite survival. Of the 11 malaria aspartyl proteases only 3 are known to be essential for survival of the blood stage form of the malaria parasite, plasmepsin V (PMV), plasmepsin IX (PMIX) and signal peptide peptidase (SPP). While inhibitors of PMV and PMIX, which have distant homology to human aspartyl proteases, may be useful as malaria therapeutics, SPP is not a reasonable drug target due to its close similarity and function to the human orthologue.

PMV is an aspartyl protease located within the parasite's endoplasmic reticulum (ER) that cleaves several hundred parasite proteins destined for export into human erythrocytes. PMV is a promising antimalarial drug target since it is essential for parasite survival in erythrocytes (Sleebs et al., *PloS Biology* 12, e1001897 (2014); Hodder et al., *Nat. Struct. Mol. Biol.* 22: 590-96 (2015)), including gametocytes.

PMV plays an essential role in the export of several hundred virulence proteins from the malaria parasite to the host erythrocyte in asexual and sexual blood stages, many of which are essential for parasite survival and development (Marti et al., Science 306(5703):1930-3 (2004); Sargeant et al., *Genome Biol.* 7:R12 (2006); Russo et al., *Nature* 463: 632-636 (2010); Boddey et al *Nature* 2010; Silvestrini et al *Mol. Cell. Proteomics* 9(7): 1437-48 (2010). Over 450 proteins are predicted to be exported via PMV, as they each contain an N-terminal export motif termed the *Plasmodium* export element (PEXEL) (Marti et al. 2004, supra) that is a cleavage site for PMV. The protein export mechanism involves processing of the PEXEL motif (RxL-*xQ/E/D) in the parasite's ER by PMV and mutations of the PEXEL sequence that block processing by PMV inhibit export to the erythrocyte (Russo et al *Nature* 2010; Boddey et al Nature 2010). The PEXEL motif and PMV are functionally conserved in all *Plasmodium* spp., including the two most virulent parasites of humans, *P. falciparum* and *P. vivax* (Sleebs et al PloS Biology 2014).

Given the development of drug-resistance by *Plasmodium* parasites, new therapies to combat malaria are urgently needed. The present invention provides compounds that are potent inhibitors of *P. falciparum* growth in vitro and may be useful for the treatment of malaria.

SUMMARY OF THE INVENTION

The present invention is directed to methods of treatment of *Plasmodium* infections comprising administering to a subject in need thereof certain N3-substituted iminopyrimidinone compounds, or a pharmaceutically acceptable salt thereof, and a pharmaceutically acceptable carrier. More specifically, the methods of the invention comprise administration of a compound of Formula (I), or a pharmaceutically acceptable salt thereof, wherein the compound has the general structure:

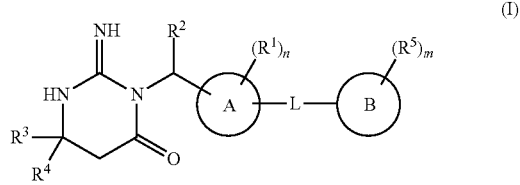

wherein:
R² is selected from the group consisting of hydrogen, halo, —C₁-C₆ alkyl, and phenyl, wherein said —C₁-C₆ alkyl and said phenyl are optionally substituted with one to three halo;
ring A is AryA or a 5- or 6-membered heterocycloalkyl;
AryA is a 5- or 6-membered monocyclic aromatic ring with 0, 1, or 2, heteroatoms independently selected from N, O and S;
each occurrence of R¹ is independently selected from halo, —CN, —OH, —C₁-C₆alkyl, —O—C₁-C₆ alkyl, —C₁-C₆haloalkyl, O—C₁-C₆ haloalkyl, and AryA;
-L- is selected from the group consisting of: —C(O)—, —C(O)—N(R^{L1})—(CH(R^{L2}))_k—,

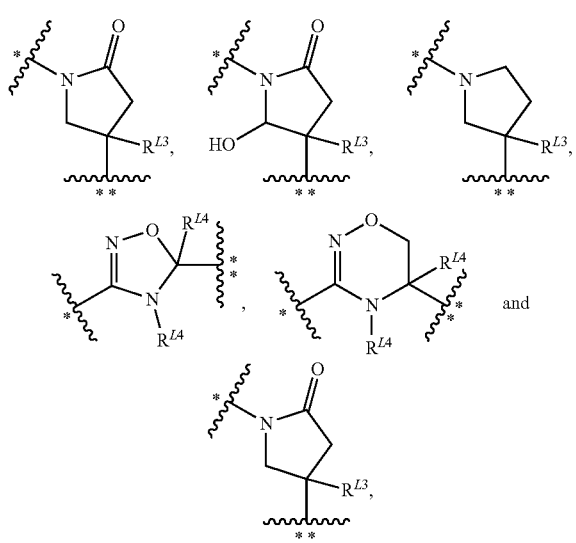

wherein:
* indicates the point of attachment to ring A and ** indicates the point of attachment to ring B, $R^{L1}$ and $R^{L3}$ (when present) are each independently selected from the group consisting of H and methyl;

$R^{L2}$ is selected from the group consisting of H, —$C_1$-$C_6$alkyl, —$C_1$-$C_6$heteroalkyl, —$C_1$-$C_3$alkyl-N($R^{L3}$)($R^{L4}$) and —$C_1$-$C_3$alkyl-N($R^{L4}$)C(O)$R^{L5}$;

$R^{L4}$ is selected from the group consisting of H and —$C_1$-$C_3$alkyl, wherein said —$C_1$-$C_3$alkyl is optionally substituted with one to three halo; and $R^{L5}$ is selected from the group consisting of H, —$C_1$-$C_3$alkyl and —$OC_1$-$C_3$alkyl, wherein said —$C_1$-$C_3$alkyl and said —$OC_1$-$C_3$alkyl are optionally substituted with one to three halo;

ring B is a $C_3$-$C_7$cycloalkyl, a $C_3$-$C_7$heterocycloalkyl, AryA, a 9- to 11-membered bicyclic aryl or a 9- to 11-membered bicyclic heteroaryl;

each occurrence of $R^5$ is independently halo, —OH, —CN, —S(O)$_z$$C_1$-$C_4$ alkyl, —C(O)($C_1$-$C_6$alkyl), —C(O)O($C_1$-$C_6$alkyl), C(O)N(H)($C_1$-$C_6$alkyl), —C(O)N($C_1$-$C_6$alkyl)$_2$, —$C_1$-$C_6$alkyl, —$C_3$-$C_6$cycloalkyl or —O$C_1$-$C_6$alkyl, wherein said —S(O)$_z$$C_1$-$C_4$ alkyl, said —C(O)($C_1$-$C_6$alkyl), —said C(O)O($C_1$-$C_6$alkyl), said C(O)N(H)($C_1$-$C_6$alkyl), said —C(O)N($C_1$-$C_6$alkyl)$_2$, said —$C_1$-$C_6$alkyl, —said $C_3$-$C_6$cycloalkyl and said —O$C_1$-$C_6$alkyl are optionally substituted with one to three substituents, independently selected from halo, —OH, —CN, or —O$C_1$-$C_6$alkyl;

$R^3$ is selected from the group consisting of:
(1) hydrogen,
(2) —$C_1$-$C_6$ alkyl,
(3) —$C_4$-$C_6$ cycloalkyl,
(4) —O—$C_1$-$C_6$alkyl,
(5) —(CH$_2$)$_n$—O—$C_1$-$C_5$alkyl, optionally substituted with one or two substituents, independently selected from halo and cyclopropyl,
(6) AryA,
(7) —(CH$_2$)$_n$-cyclopropyl, wherein each of said —$C_1$-$C_6$ alkyl, said —$C_4$-$C_6$ cycloalkyl, said —O—$C_1$-$C_6$alkyl, and said —(CH$_2$)$_n$-cyclopropyl are optionally substituted with one or two substituents, independently selected from halo, —OH, and —O—$C_1$-$C_6$alkyl, and wherein said AryA is optionally substituted with one to three substituents, independently selected from —OH, halo, —O—$C_1$-$C_6$alkyl, $C_1$-$C_6$fluoroalkyl, —CN, OCF$_3$, OCF$_2$, and —S(=O)$_k$—$C_1$-$C_6$alkyl;

$R^4$ is selected from the group consisting of hydrogen, —$C_1$-$C_6$alkyl, and AryA, wherein said —$C_1$-$C_6$alkyl and said Ary A are optionally substituted with one to three substitutents, independently selected from halo, —OH, —O—$C_1$-$C_3$alkyl, —$C_1$-$C_3$alkyl and cyclopropyl;

alternatively, $R^3$ and $R^4$, together with the carbon to which they are attached, join to form a 4- or 5- or 6-membered spirocyclic cycloalkyl, optionally substituted with one or two substitutents, independently selected from halo, —OH, —O—$C_1$-$C_3$alkyl, and —$C_1$-$C_3$alkyl;

n is 0, 1, 2, or 3;
m is 0, 1, 2, 3, 4, 5, or 6;
k is 0 or 1; and
z is 1 or 2.

The compounds, and their pharmaceutically acceptable salts, can be useful, for example, for the treatment of malaria. The compounds of Formula (I) are able to impair the proteolytic function of plasmepsin V, which disrupts parasite growth.

The present invention further provides the use of compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent, for the treatment of malaria.

Moreover, the present invention provides methods for the use of pharmaceutical compositions comprising one or more of said compounds in the free form or in pharmaceutically acceptable salt form, together with one or more customary pharmaceutical excipient(s), for the treatment of *Plasmodium* infections, the treatment of malaria, or the inhibition of plasmepsin V. Methods for the use of combinations of the compounds or salts of the invention together with one or more additional pharmaceutically active agents are also provided.

The present invention further provides methods for the inhibition of plasmepsin V activity and of treatment, prevention, amelioration and/or delaying onset of diseases or disorders in which the inhibition of plasmepsinV has or may have a therapeutic effect, e.g. malaria.

These and other embodiments of the invention, which are described in detail below or will become readily apparent to those of ordinary skill in the art, are included within the scope of the invention.

DETAILED DESCRIPTION OF THE INVENTION

The present invention is directed to methods of treatment of *Plasmodium* infections comprising administering to a subject in need thereof certain N3-substituted iminopyrimidinone compounds, or a pharmaceutically acceptable salt thereof. More specifically, the methods of the invention comprise administration of a compound of Formula (I), or a pharmaceutically acceptable salt thereof, wherein the compound has the general structure:

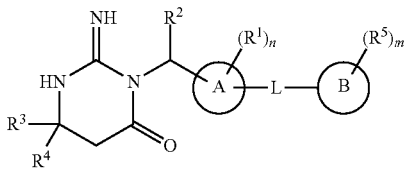

(I)

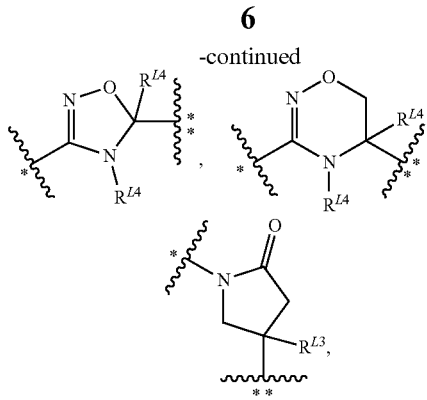

wherein $R^1$, $R^2$, $R^3$, $R^4$, $R^5$, A, L, B, m and n are defined in the Summary of the Invention, and further defined herein. In certain embodiments, the compounds of Formula (I), or a pharmaceutically acceptable salt thereof, are administered in the form of a pharmaceutical composition, further comprising a pharmaceutically acceptable carrier or excipient.

In each of the various embodiments of the invention, in the compounds used in the methods herein, each variable (including those in each of Formula (I), (IA), (IB), and (IC), and the various embodiments thereof) it shall be understood that each variable is to be selected independently of the others unless otherwise indicated.

In each of the various embodiments of the invention, the compounds described herein, including those in each of Formula (I), (IA), (IB), and (IC) and the various embodiments thereof, may exit in different forms of the compounds such as, for example, any solvates, hydrates, stereoisomers, and tautomers of said compounds and of any pharmaceutically acceptable salts thereof.

In one embodiment, the compounds used in the methods of the invention have the general structure shown in Formula (I):

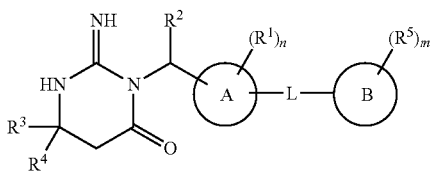

(I)

or a pharmaceutically acceptable salt thereof, wherein:
  $R^2$ is selected from the group consisting of hydrogen, halo, —$C_1$-$C_6$ alkyl, and phenyl, wherein said —$C_1$-$C_6$ alkyl and said phenyl are optionally substituted with one to three halo;
  ring A is AryA or a 5- or 6-membered heterocycloalkyl;
  AryA is a 5- or 6-membered monocyclic aromatic ring with 0, 1, or 2, heteroatoms independently selected from N, O and S;
  each occurrence of $R^1$ is independently selected from halo, —CN, —OH, —$C_1$-$C_6$alkyl, —O—$C_1$-$C_6$ alkyl, —$C_1$-$C_6$haloalkyl, O—$C_1$-$C_6$ haloalkyl, and AryA;
  -L- is selected from the group consisting of: —C(O)—, —C(O)—N($R^{L1}$)—(CH($R^{L2}$))$_k$—,

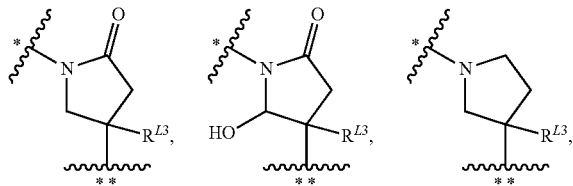

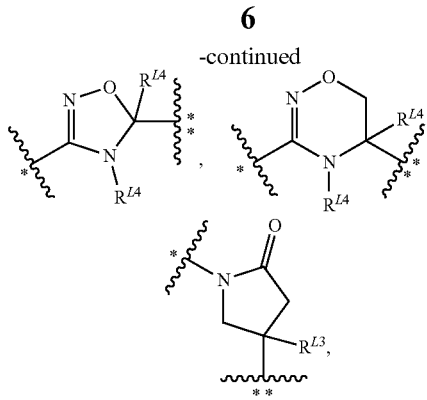 and wherein:
  * indicates the point of attachment to ring A and ** indicates the point of attachment to ring B,
  $R^{L1}$ and $R^{L3}$ (when present) are each independently selected from the group consisting of H and methyl;
  $R^{L2}$ is selected from the group consisting of H, —$C_1$-$C_6$alkyl, —$C_1$-$C_6$heteroalkyl, —$C_1$-$C_3$alkyl-N($R^{L3}$)($R^{L4}$) and —$C_1$-$C_3$alkyl-N($R^{L4}$)C(O)$R^{L5}$;
  $R^{L4}$ is selected from the group consisting of H and —$C_1$-$C_3$alkyl, wherein said —$C_1$-$C_3$alkyl is optionally substituted with one to three halo; and
  $R^{L5}$ is selected from the group consisting of H, —$C_1$-$C_3$alkyl and —O$C_1$-$C_3$alkyl, wherein said —$C_1$-$C_3$alkyl and said —O$C_1$-$C_3$alkyl are optionally substituted with one to three halo;
  ring B is a $C_3$-$C_7$cycloalkyl, a $C_3$-$C_7$heterocycloalkyl, AryA, a 9- to 11-membered bicyclic aryl or a 9- to 11-membered bicyclic heteroaryl;
  each occurrence of $R^5$ is independently halo, —OH, —CN, —S(O)$_z$$C_1$-$C_4$ alkyl, —C(O)($C_1$-$C_6$alkyl), —C(O)O($C_1$-$C_6$alkyl), C(O)N(H)($C_1$-$C_6$alkyl), —C(O)N($C_1$-$C_6$alkyl)$_2$, —$C_1$-$C_6$alkyl, —$C_3$-$C_6$cycloalkyl or —O$C_1$-$C_6$alkyl, wherein said —S(O)$_z$ $C_1$-$C_4$ alkyl, said —C(O)($C_1$-$C_6$alkyl), —said C(O)O ($C_1$-$C_6$alkyl), said C(O)N(H)($C_1$-$C_6$alkyl), said —C(O)N($C_1$-$C_6$alkyl)$_2$, said —$C_1$-$C_6$alkyl, —said $C_3$-$C_6$cycloalkyl and said —O$C_1$-$C_6$alkyl are optionally substituted with one to three substituents, independently selected from halo, —OH, —CN, or —O$C_1$-$C_6$alkyl;
  $R^3$ is selected from the group consisting of:
    (1) hydrogen,
    (2) —$C_1$-$C_6$ alkyl,
    (3) —$C_4$-$C_6$ cycloalkyl,
    (4) —O—$C_1$-$C_6$alkyl,
    (5) —(CH$_2$)$_n$—O—$C_1$-$C_5$alkyl, optionally substituted with one or two substituents, independently selected from halo and cyclopropyl,
    (6) AryA,
    (7) —(CH$_2$)$_n$-cyclopropyl,
  wherein each of said —$C_1$-$C_6$ alkyl, said —$C_4$-$C_6$ cycloalkyl, said —O—$C_1$-$C_6$alkyl, and said —(CH$_2$)$_n$-cyclopropyl are optionally substituted with one or two substituents, independently selected from halo, —OH, and —O—$C_1$-$C_6$alkyl, and wherein said AryA is optionally substituted with one to three substituents, independently selected from —OH, halo, —O—$C_1$-$C_6$alkyl, $C_1$-$C_6$fluoroalkyl, —CN, OCF$_3$, OCF$_2$, and —S(=O)$_k$—$C_1$-$C_6$alkyl;
  $R^4$ is selected from the group consisting of hydrogen, —$C_1$-$C_6$alkyl, and AryA, wherein said —$C_1$-$C_6$alkyl and said Ary A are optionally substituted with one to three substitutents, independently selected from halo, —OH, —O—$C_1$-$C_3$alkyl, —$C_1$-$C_3$alkyl and cyclopropyl;

alternatively, $R^3$ and $R^4$, together with the carbon to which they are attached, join to form a 4- or 5- or 6-membered spirocyclic cycloalkyl, optionally substituted with one or two substitutents, independently selected from halo, —OH, —O—$C_1$-$C_3$alkyl, and —$C_1$-$C_3$alkyl;

n is 0, 1, 2, or 3;
m is 0, 1, 2, 3, 4, 5, or 6;
k is 0 or 1; and
z is 1 or 2.

In a particular sub-embodiment of Formula (I) are compounds of Formula (I) wherein A method for treating a *Plasmodium* infection, or for treating malaria, which comprises administering to a subject in need of such treatment a therapeutically effective amount of a compound, and a pharmaceutically acceptable carrier, said compound having the structural Formula (I):

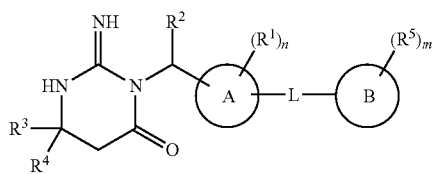

(I)

or a pharmaceutically acceptable salt of said compound, wherein:

$R^2$ is selected from the group consisting of hydrogen, halo, —$C_1$-$C_6$ alkyl, and phenyl, wherein said —$C_1$-$C_6$ alkyl and said phenyl are optionally substituted with one to three halo;

ring A is AryA or a 5- or 6-membered heterocycloalkyl;

AryA is a 5- or 6-membered monocyclic aromatic ring with 0, 1, or 2, heteroatoms independently selected from N, O and S;

each occurrence of $R^1$ is independently selected from halo, —CN, —OH, —$C_1$-$C_6$alkyl, —O—$C_1$-$C_6$ alkyl, O—$C_1$-$C_6$ haloalkyl, —$C_1$-$C_6$haloalkyl and AryA;

-L- is selected from the group consisting of: —C(O)—, —C(O)—N($R^{L1}$)—(CH($R^{L2}$))$_k$—,

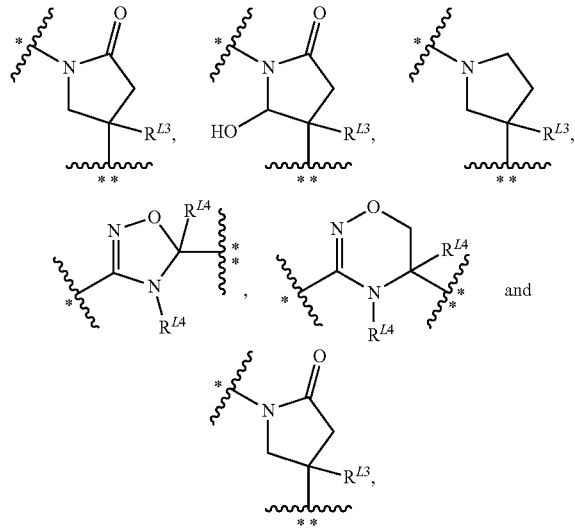

wherein:
* indicates the point of attachment to ring A and ** indicates the point of attachment to ring B, $R^{L1}$ and $R^{L3}$ (when present) are each independently selected from the group consisting of H and methyl;

$R^{L2}$ is selected from the group consisting of H, —$C_1$-$C_6$alkyl, —$C_1$-$C_6$heteroalkyl, and —$C_1$-$C_3$alkyl-N($R^{L4}$)C(O)$R^{L5}$;

$R^{L4}$ is selected from the group consisting of H and —$C_1$-$C_3$alkyl, wherein said —$C_1$-$C_3$alkyl is optionally substituted with one to three halo; and $R^{L5}$ is selected from the group consisting of H, —$C_1$-$C_3$alkyl and —O$C_1$-$C_3$alkyl, wherein said —$C_1$-$C_3$alkyl and said —O$C_1$-$C_3$alkyl are optionally substituted with one to three halo;

ring B is a $C_3$-$C_7$cycloalkyl, a $C_3$-$C_7$heterocycloalkyl, AryA, a 9- to 11-membered bicyclic aryl or a 9- to 11-membered bicyclic heteroaryl;

each occurrence of $R^5$ is independently halo, —OH, —CN, —S(O)$_z$$C_1$-$C_4$ alkyl, —C(O)($C_1$-$C_6$alkyl), —C(O)O($C_1$-$C_6$alkyl), C(O)N(H)($C_1$-$C_6$alkyl), —C(O)N($C_1$-$C_6$alkyl)$_2$, —$C_1$-$C_6$alkyl, —$C_3$-$C_6$cycloalkyl or —O$C_1$-$C_6$alkyl, wherein said —S(O)$_z$ $C_1$-$C_4$ alkyl, said —C(O)($C_1$-$C_6$alkyl), —said C(O)O ($C_1$-$C_6$alkyl), said C(O)N(H)($C_1$-$C_6$alkyl), said —C(O)N($C_1$-$C_6$alkyl)$_2$, said —$C_1$-$C_6$alkyl, —said $C_3$-$C_6$cycloalkyl and said —O$C_1$-$C_6$alkyl are optionally substituted with one to three substituents, independently selected from halo, —OH, —CN, or —O$C_1$-$C_6$alkyl;

$R^3$ is selected from the group consisting of:
(1) hydrogen,
(2) —$C_1$-$C_6$ alkyl,
(3) —$C_4$-$C_6$ cycloalkyl,
(4) —O—$C_1$-$C_6$alkyl,
(5) —(CH$_2$)$_n$—O—$C_1$-$C_5$alkyl, optionally substituted with one or two substituents, independently selected from halo and cyclopropyl,
(6) AryA,
(7) —(CH$_2$)$_n$-cyclopropyl, wherein each of said —$C_1$-$C_6$ alkyl, said —$C_4$-$C_6$ cycloalkyl, said —O—$C_1$-$C_6$alkyl, and said —(CH$_2$)$_n$-cyclopropyl are optionally substituted with one or two substituents, independently selected from halo, —OH, and —O—$C_1$-$C_6$alkyl, and wherein said AryA is optionally substituted with one to three substituents, independently selected from —OH, halo, —O—$C_1$-$C_6$alkyl, $C_1$-$C_6$fluoroalkyl, —CN, OCF$_3$, OCF$_2$, and —S(═O)$_k$—$C_1$-$C_6$alkyl;

$R^4$ is selected from the group consisting of hydrogen, —$C_1$-$C_6$alkyl, and AryA, wherein said —$C_1$-$C_6$alkyl and said Ary A are optionally substituted with one to three substitutents, independently selected from halo, —OH, —O—$C_1$-$C_3$alkyl, —$C_1$-$C_3$alkyl and cyclopropyl;

alternatively, $R^3$ and $R^4$, together with the carbon to which they are attached, join to form a 4- or 5- or 6-membered spirocyclic cycloalkyl, optionally substituted with one or two substitutents, independently selected from halo, —OH, —O—$C_1$-$C_3$alkyl, and —$C_1$-$C_3$alkyl;

n is 0, 1, 2, or 3;
m is 0, 1, 2, or 3;
k is 0 or 1; and
z is 1 or 2.

The present invention provides a method for treating a *Plasmodium* infection, or for treating malaria, or for inhibiting plasmepsin V, which comprises administering to a subject in need of such treatment a therapeutically effective amount of a compound, or a pharmaceutically acceptable salt thereof, said compound having the structural Formula (I) described in the Summary of the Invention. In some embodiments, the compounds of Formula (I), or pharmaceutically acceptable salts thereof, are administered with a pharmaceutically acceptable carrier, as a pharmaceutical composition. Also provided herein are various embodiments of these methods, as described, infra.

The invention also relates to the use of a compound of Formula (I), (IA), (IB), or (IC) or a pharmaceutically acceptable salt thereof for inhibiting plasmepsin V activity, for treating a *Plasmodium* infection, or for treating malaria. The invention further relates to the use of a compound of Formula (I), (IA), (IB), or (IC) or a pharmaceutically acceptable salt thereof in the manufacture of a medicament for inhibiting plasmepsin V activity, for treating a *Plasmodium* infection, or for treating malaria. The compounds of Formula (I), (IA), (IB), or (IC) or pharmaceutically acceptable salts thereof described in any of the embodiments of the invention herein are useful for any of the uses above.

The methods of the present invention are useful for treating malaria in that they inhibit the onset, growth, or progression of the condition, ameliorate the symptoms of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject of infection, such as in a subject that has been exposed to a parasite as disclosed herein.

Embodiments of the invention also include one or more of the compounds of Formula (I), (IA), (IB), or (IC) or a pharmaceutically acceptable salt thereof (i) for use in, (ii) for use as a medicament or composition for, or (iii) for use in the preparation of a medicament for: (a) therapy (e.g., of the human body); (b) medicine; (c) inhibition of parasite/*Plasmodium* growth, (d) treatment or prophylaxis of infection by *Plasmodium* species; (e) reduction of the progression, onset or severity of pathological symptoms associated with *Plasmodium* infection and/or reduction of the likelihood of severe *Plasmodium* infection or, (f) treatment, prophylaxis of, or delay in the onset, severity, or progression of *Plasmodium*-associated disease(s), including, but not limited to: malaria.

A first embodiment of the methods of the invention (Embodiment E1) comprises administration of a compound of Formula (I), or a pharmaceutically acceptable salt thereof, wherein $R^1$, $R^2$, $R^3$, $R^4$, $R^5$, A, B, L, m and n are as originally defined (i.e. as defined in Formula (I) in the Summary of the Invention).

A second embodiment of the methods of the invention (Embodiment E2) comprises administration of a compound of Formula (I), or a pharmaceutically acceptable salt thereof, wherein $R^2$ is hydrogen, and all other variables are as defined in Embodiment E1.

A third embodiment of the methods of the invention (Embodiment E3) comprises administration of a compound of Formula (I), or a pharmaceutically acceptable salt thereof, wherein $R^2$ is halo, and all other variables are as defined in Embodiment E1.

A fourth embodiment of the methods of the invention (Embodiment E4) comprises administration of a compound of Formula (I), or a pharmaceutically acceptable salt thereof, wherein $R^2$ is —$C_1$-$C_6$ alkyl, optionally substituted with one to three halo, and all other variables are as defined in Embodiment E1.

A fifth embodiment of the methods of the invention (Embodiment E5) comprises administration of a compound of Formula (I), or a pharmaceutically acceptable salt thereof, wherein $R^2$ is methyl, and all other variables are as defined in Embodiment E1.

A sixth embodiment of the methods of the invention (Embodiment E6) comprises administration of a compound of Formula (I), or a pharmaceutically acceptable salt thereof, wherein $R^2$ is phenyl, which is unsubstituted, and all other variables are as defined in Embodiment E1.

A seventh embodiment of the methods of the invention (Embodiment E7) comprises administration of a compound of Formula (I), or a pharmaceutically acceptable salt thereof, wherein $R^2$ is phenyl, substituted with one to three halo, and all other variables are as defined in Embodiment E1.

An eighth embodiment of the methods of the invention (Embodiment E8) comprises administration of a compound of Formula (I), or a pharmaceutically acceptable salt thereof, wherein $R^2$ is as defined in any of Embodiments E1-E7, ring A is AryA, wherein AryA is a 5- or 6-membered monocyclic aromatic ring with 0, 1, or 2, heteroatoms independently selected from N, O and S, and all other variables are as defined in Embodiment E1.

In a sub-embodiment of Embodiment E8, AryA is a 5-membered aryl. In another sub-embodiment of Embodiment E8, AryA is a 6-membered aryl. In yet another sub-embodiment of Embodiment E8, AryA is a 5-membered heteroaryl. In a further sub-embodiment of Embodiment E8, AryA is a 6-membered heteroaryl.

A ninth embodiment of the methods of the invention (Embodiment E9) comprises administration of a compound of Formula (I), or a pharmaceutically acceptable salt thereof, wherein $R^2$ is as defined in any of Embodiments E1-E7, ring A is a 5- or 6-membered heterocycloalkyl, and all other variables are as defined in Embodiment E1.

A tenth embodiment of the methods of the invention (Embodiment E10) comprises administration of a compound of Formula (I), or a pharmaceutically acceptable salt thereof, wherein $R^2$ is as defined in any of Embodiments E1-E7, A is phenyl, and all other variables are as defined in Embodiment E1.

An eleventh embodiment of the methods of the invention (Embodiment E11) comprises administration of a compound of Formula (I), or a pharmaceutically acceptable salt thereof, wherein $R^2$ is as defined in any of Embodiments E1-E7, ring A is:

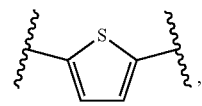 [SMILES: *c1ccc(*)s1]

and all other variables are as defined in Embodiment E1.

In sub-embodiments of Embodiments E8-E11, ring A is unsubstituted.

In further sub-embodiments of Embodiments E8-E11, ring A is substituted with one to three occurrences of $R^1$, which are independently selected from halo, —CN, —OH, —$C_1$-$C_6$alkyl, —O—$C_1$-$C_6$ alkyl, —$C_1$-$C_6$haloalkyl, O—$C_1$-$C_6$ haloalkyl, and AryA.

In some sub-embodiments of Embodiments E8-E11, ring A is substituted with one to three halo. In a sub-sub-embodiment, the substituent is F or Cl.

In some sub-embodiments of Embodiments E8-E11, ring A is substituted with one to three —CN.

In further sub-embodiments of Embodiments E8-E11, ring A is substituted with one to three —OH.

In other sub-embodiments of Embodiments E8-E11, ring A is substituted with one to three —$C_1$-$C_6$alkyl.

In still other sub-embodiments of Embodiments E8-E11, ring A is substituted with one to three —O—$C_1$-$C_6$ alkyl.

In further sub-embodiments of Embodiments E8-E11, ring A is substituted with one to three —$C_1$-$C_6$haloalkyl. In a sub-sub-embodiment, the substituent is $CF_3$.

In further sub-embodiments of Embodiments E8-E11, ring A is substituted with one to three —O—$C_1$-$C_6$haloalkyl. In a sub-sub-embodiment, the substituent is O—$CF_3$.

In additional sub-embodiments of Embodiments E8-E11, ring A is substituted with one to three AryA. In a sub-sub-embodiment, the substituent is phenyl.

It is to be understood that the substituents on ring A in the above sub-embodiments can be combined with any other sub-embodiment, e.g., ring A can be substituted with halo and methyl.

A twelfth embodiment of the methods of the invention (Embodiment E12) comprises administration of a compound of Formula (I), or a pharmaceutically acceptable salt thereof, wherein $R^2$ is as defined in any of Embodiments E1-E7, ring A is defined in any of embodiments E8-E11, -L- is —C(O)— and all other variables are as defined in Embodiment E1.

A thirteenth embodiment of the methods of the invention (Embodiment E13) comprises administration of a compound of Formula (I), or a pharmaceutically acceptable salt thereof, wherein $R^2$ is as defined in any of Embodiments E1-E7, ring A is defined in any of embodiments E8-E11, -L- is —C(O)—N($R^{L1}$)—(CH($R^{L2}$))$_k$—, and all other variables are as defined in Embodiment E1.

A fourteenth embodiment of the methods of the invention (Embodiment E14) comprises administration of a compound of Formula (I), or a pharmaceutically acceptable salt thereof, wherein $R^2$ is as defined in any of Embodiments E1-E7, ring A is defined in any of embodiments E8-E11, -L- is selected from the group consisting of:

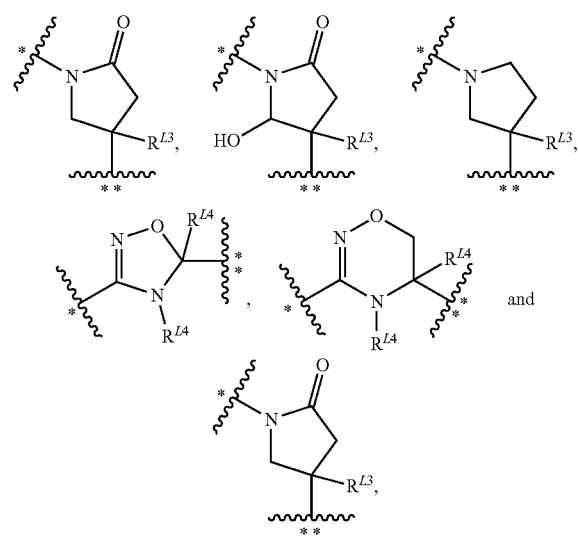

wherein:
* indicates the point of attachment to ring A and ** indicates the point of attachment to ring B, $R^{L3}$ (when present) is independently selected from the group consisting of H and methyl, and $R^{L4}$ (when present) is selected from the group consisting of H and —$C_1$-$C_3$alkyl, wherein said —$C_1$-$C_3$alkyl is optionally substituted with one to three halo; and all other variables are as defined in Embodiment E1.

A fifteenth embodiment of the methods of the invention (Embodiment E15) comprises administration of a compound of Formula (I), or a pharmaceutically acceptable salt thereof, wherein $R^2$ is as defined in any of Embodiments E1-E7, ring A is defined in any of embodiments E8-E11, -L- is

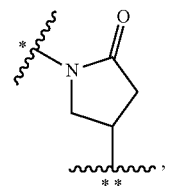 [SMILES: *C1CC(=O)N(*)C1]

wherein * indicates the point of attachment to ring A and ** indicates the point of attachment to ring B, and all other variables are as defined in Embodiment E1.

A sixteenth embodiment of the methods of the invention (Embodiment E16) comprises administration of a compound of Formula (I), or a pharmaceutically acceptable salt thereof, wherein $R^2$ is as defined in any of Embodiments E1-E7, ring A is defined in any of embodiments E8-E11, -L- is —C(O)—N(H)—(CH(CH$_3$))—, and all other variables are as defined in Embodiment E1.

A seventeenth embodiment of the methods of the invention (Embodiment E17) comprises administration of a compound of Formula (I), or a pharmaceutically acceptable salt thereof, wherein $R^2$ is as defined in any of Embodiments E1-E7, ring A is defined in any of embodiments E8-E11, -L- is —C(O)—N(H)—, and all other variables are as defined in Embodiment E1.

An eighteenth embodiment of the methods of the invention (Embodiment E18) comprises administration of a compound of Formula (I), or a pharmaceutically acceptable salt thereof, wherein $R^2$ is as defined in any of Embodiments E1-E7, ring A is defined in any of embodiments E8-E11, -L- is —C(O)—N(H)—(CH(—$C_1$-$C_6$heteroalkyl))-, and all other variables are as defined in Embodiment E1.

A nineteenth embodiment of the methods of the invention (Embodiment E19) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is a $C_3$-$C_7$cycloalkyl, a $C_3$-$C_7$heterocycloalkyl, AryA, a 9- to 11-membered bicyclic aryl or a 9- to 11-membered bicyclic heteroaryl; and all other variables are as defined in Embodiment E1.

A twentieth embodiment of the methods of the invention (Embodiment E20) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is a $C_3$-$C_7$cycloalkyl, and all other variables are as defined in Embodiment E1.

A twenty-first embodiment of the methods of the invention (Embodiment E21) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is a $C_3$-$C_7$heterocycloalkyl, and all other variables are as defined in Embodiment E1.

A twenty-second embodiment of the methods of the invention (Embodiment E22) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is AryA, and all other variables are as defined in Embodiment E1.

A twenty-third embodiment of the methods of the invention (Embodiment E23) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is a 9- to 11-membered bicyclic aryl, and all other variables are as defined in Embodiment E1.

A twenty-fourth embodiment of the methods of the invention (Embodiment E24) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is a 9- to 11-membered bicyclic heteroaryl; and all other variables are as defined in Embodiment E1.

A twenty-fifth embodiment of the methods of the invention (Embodiment E25) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is phenyl and all other variables are as defined in Embodiment E1.

In sub-embodiments of Embodiments E19-E25, ring B is unsubstituted.

In further sub-embodiments of Embodiments E19-E25, ring B is substituted with one to six occurrences of $R^5$ independently selected from halo, —OH, —CN, —S(O)$_z$C$_1$-C$_4$ alkyl, —C(O)(C$_1$-C$_6$alkyl), —C(O)O(C$_1$-C$_6$alkyl), C(O)N(H)(C$_1$-C$_6$alkyl), —C(O)N(C$_1$-C$_6$alkyl)$_2$, —C$_1$-C$_6$alkyl, —C$_3$-C$_6$cycloalkyl or —OC$_1$-C$_6$alkyl, wherein said —S(O)$_z$C$_1$-C$_4$ alkyl, said —C(O)(C$_1$-C$_6$alkyl), —said C(O)O(C$_1$-C$_6$alkyl), said C(O)N(H)(C$_1$-C$_6$alkyl), said —C(O)N(C$_1$-C$_6$alkyl)$_2$, said —C$_1$-C$_6$alkyl, —said C$_3$-C$_6$cycloalkyl and said —OC$_1$-C$_6$alkyl are optionally substituted with one to three substituents, independently selected from halo, —OH, —CN, or —OC$_1$-C$_6$alkyl.

In some sub-embodiments of Embodiments E19-E25, ring B is substituted with one to three halo.

In some sub-embodiments of Embodiments E19-E25, ring B is substituted with —C$_1$-C$_6$alkyl optionally substituted with one to three halo.

A twenty-sixth embodiment of the methods of the invention (Embodiment E26) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is selected from the group consisting of:

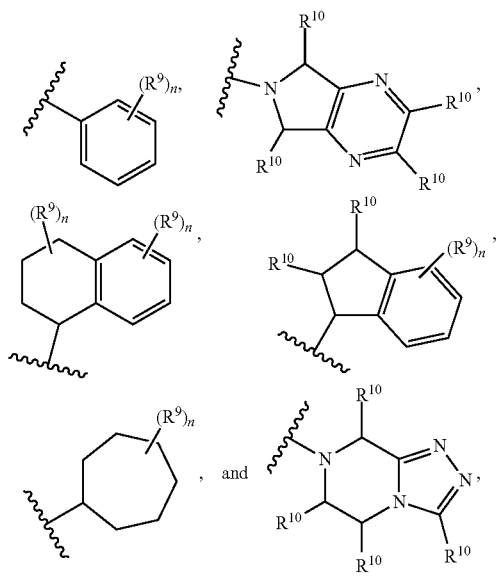

wherein each occurrence of $R^9$ is independently selected from H, halo, and C$_1$-C$_6$alkyl; and each occurrence of $R^{10}$ is independently selected from H, halo, and CF$_3$, and all other variables are as defined in Embodiment E1.

A twenty-seventh embodiment of the methods of the invention (Embodiment E27) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is:

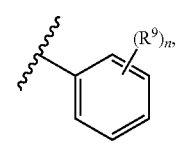

and all other variables are as defined in Embodiment E1.

A twenty-eighth embodiment of the methods of the invention (Embodiment E28) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is:

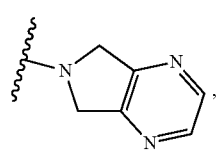 [SMILES: *N1Cc2nccnc2C1]

and all other variables are as defined in Embodiment E1.

A twenty-ninth embodiment of the methods of the invention (Embodiment E29) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is:

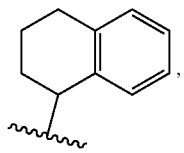 [SMILES: *C1CCCc2ccccc21]

and all other variables are as defined in Embodiment E1.

A thirtieth embodiment of the methods of the invention (Embodiment E30) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is:

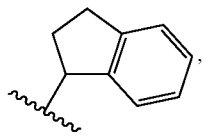 [SMILES: *C1CCc2ccccc21]

and all other variables are as defined in Embodiment E1.

A thirty-first embodiment of the methods of the invention (Embodiment E31) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is:

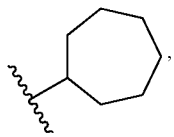 [SMILES: *C1CCCCCC1]

and all other variables are as defined in Embodiment E1.

A thirty-second embodiment of the methods of the invention (Embodiment E32) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is:

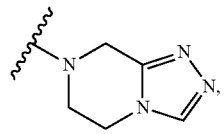 [SMILES: *N1CCn2cnnc2C1]

and all other variables are as defined in Embodiment E1.

A thirty-third embodiment of the methods of the invention (Embodiment E33) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is as defined in any of Embodiments E19-E32, $R^3$ is hydrogen, and all other variables are as defined in Embodiment E1.

A thirty-fourth embodiment of the methods of the invention (Embodiment E34) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is as defined in any of Embodiments E19-E32, $R^3$ is —$C_1$-$C_6$ alkyl, optionally substituted with one or two substituents, independently selected from halogen, —OH, and —O—$C_1$-$C_6$alkyl, and all other variables are as defined in Embodiment E1.

A thirty-fifth embodiment of the methods of the invention (Embodiment E35) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is as defined in any of Embodiments E19-E32, $R^3$ is —$C_4$-$C_6$ cycloalkyl, optionally substituted with one or two substituents, independently selected from halogen, —OH, and —O—$C_1$-$C_6$alkyl, and all other variables are as defined in Embodiment E1.

A thirty-sixth embodiment of the methods of the invention (Embodiment E36) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is as defined in any of Embodiments E19-E32, $R^3$ is —O—$C_1$-$C_6$alkyl, optionally substituted with one or two substituents, independently selected from halogen, —OH, and —O—$C_1$-$C_6$alkyl, and all other variables are as defined in Embodiment E1.

A thirty-seventh embodiment of the methods of the invention (Embodiment E37) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is as defined in any of Embodiments E19-E32, $R^3$ is —$(CH_2)_n$—O—$C_1$-$C_6$alkyl, optionally substituted with one or two substituents, independently selected from halo and cyclopropyl, and all other variables are as defined in Embodiment E1.

A thirty-eighth embodiment of the methods of the invention (Embodiment E38) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is as defined in any of Embodiments E19-E32, $R^3$ is AryA, optionally substituted with one to three substituents, independently selected from —OH, halo, —O—$C_1$-$C_6$alkyl, $C_1$-$C_6$fluoroalkyl, —CN, $OCF_3$, $OCF_2$, and —$S(=O)_k$—$C_1$-$C_6$alkyl, and all other variables are as defined in Embodiment E1.

A thirty-ninth embodiment of the methods of the invention (Embodiment E39) comprises administration of a compound of Formula (I), or a pharmaceutically acceptable salt thereof, wherein $R^2$ is as defined in any of Embodiments E1-E7, ring A is defined in any of embodiments E8-E11, -L- is as defined in any of Embodiments E12-E18, ring B is as defined in any of Embodiments E19-E32, $R^3$ is —$(CH_2)_n$-cyclopropyl, optionally substituted with one or two substituents, independently selected from halogen, —OH, and —O—$C_1$-$C_6$alkyl, and all other variables are as defined in Embodiment E1.

A fortieth embodiment of the methods of the invention (Embodiment E40) comprises administration of a compound of Formula (I), or a pharmaceutically acceptable salt thereof, wherein $R^2$ is as defined in any of Embodiments E1-E7, ring A is defined in any of Embodiments E8-E11, -L- is as defined in any of Embodiments E12-E18, ring B is as defined in any of Embodiments E19-E32, R³ is phenyl optionally substituted with one to three halo, and all other variables are as defined in Embodiment E1.

A forty-first embodiment of the methods of the invention (Embodiment E41) comprises administration of a compound of Formula (I), or a pharmaceutically acceptable salt thereof, wherein R² is as defined in any of Embodiments E1-E7, ring A is defined in any of embodiments E8-E11, -L- is as defined in any of Embodiments E12-E18, ring B is as defined in any of Embodiments E19-E32, R³ is methyl, and all other variables are as defined in Embodiment E1.

A forty-second embodiment of the methods of the invention (Embodiment E42) comprises administration of a compound of Formula (I), or a pharmaceutically acceptable salt thereof, wherein R² is as defined in any of Embodiments E1-E7, ring A is defined in any of embodiments E8-E11, -L- is as defined in any of Embodiments E12-E18, ring B is as defined in any of Embodiments E19-E32, R³ is isopropyl, and all other variables are as defined in Embodiment E1.

A forty-third embodiment of the methods of the invention (Embodiment E43) comprises administration of a compound of Formula (I), or a pharmaceutically acceptable salt thereof, wherein R² is as defined in any of Embodiments E1-E7, ring A is defined in any of embodiments E8-E11, -L- is as defined in any of Embodiments E12-E18, ring B is as defined in any of Embodiments E19-E32, R³ is as defined in any of Embodiments E33-E42, R⁴ is hydrogen, and all other variables are as defined in Embodiment E1.

A forty-fourth embodiment of the methods of the invention (Embodiment E44) comprises administration of a compound of Formula (I), or a pharmaceutically acceptable salt thereof, wherein R² is as defined in any of Embodiments E1-E7, ring A is defined in any of embodiments E8-E11, -L- is as defined in any of Embodiments E12-E18, ring B is as defined in any of Embodiments E19-E32, R³ is as defined in any of Embodiments E33-E42, R⁴ is —C₁-C₆alkyl, optionally substituted with one to three substitutents, independently selected from halo, —OH, —O—C₁-C₃alkyl, —C₁-C₃alkyl and cyclopropyl, and all other variables are as defined in Embodiment E1.

A forty-fifth embodiment of the methods of the invention (Embodiment E45) comprises administration of a compound of Formula (I), or a pharmaceutically acceptable salt thereof, wherein R² is as defined in any of Embodiments E1-E7, ring A is defined in any of embodiments E8-E11, -L- is as defined in any of Embodiments E12-E18, ring B is as defined in any of Embodiments E19-E32, R³ is as defined in any of Embodiments E33-E42, R⁴ is AryA, optionally substituted with one to three substitutents, independently selected from halo, —OH, —O—C₁-C₃alkyl, —C₁-C₃alkyl and cyclopropyl, and all other variables are as defined in Embodiment E1.

A forty-sixth embodiment of the methods of the invention (Embodiment E46) comprises administration of a compound of Formula (I), or a pharmaceutically acceptable salt thereof, wherein R² is as defined in any of Embodiments E1-E7, ring A is defined in any of embodiments E8-E11, -L- is as defined in any of Embodiments E12-E18, ring B is as defined in any of Embodiments E19-E32, R³ is as defined in any of Embodiments E33-E42, R⁴ is methyl, and all other variables are as defined in Embodiment E1.

A forty-seventh embodiment of the methods of the invention (Embodiment E47) comprises administration of a compound of Formula (I), or a pharmaceutically acceptable salt thereof, wherein R² is as defined in any of Embodiments E1-E7, ring A is defined in any of embodiments E8-E11, -L- is as defined in any of Embodiments E12-E18, ring B is as defined in any of Embodiments E19-E32, R³ is as defined in any of Embodiments E33-E42, R⁴ is phenyl optionally substituted with one to three halo, and all other variables are as defined in Embodiment E1.

A forty-eighth embodiment of the methods of the invention (Embodiment E48) comprises administration of a compound of Formula (I), or a pharmaceutically acceptable salt thereof, wherein R² is as defined in any of Embodiments E1-E7, ring A is defined in any of embodiments E8-E11, -L- is as defined in any of Embodiments E12-E18, ring B is as defined in any of Embodiments E19-E32, R³ is as defined in any of Embodiments E33-E42, R⁴ is —(CH₂)ₙ-cyclopropyl, and all other variables are as defined in Embodiment E1.

A forty-ninth embodiment of the methods of the invention (Embodiment E49) comprises administration of a compound of Formula (I), or a pharmaceutically acceptable salt thereof, wherein R² is as defined in any of Embodiments E1-E7, ring A is defined in any of embodiments E8-E11, -L- is as defined in any of Embodiments E12-E18, ring B is as defined in any of Embodiments E19-E32, and R³ and R⁴, together with the carbon to which they are attached, join to form a 4- or 5- or 6-membered spirocyclic cycloalkyl, optionally substituted with one or two substitutents, independently selected from halo, —OH, —O—C₁-C₃alkyl, and —C₁-C₃alkyl, and all other variables are as defined in Embodiment E1.

A fiftieth embodiment of the methods of the invention (Embodiment E50) comprises administration of a compound of Formula (I), or a pharmaceutically acceptable salt thereof, wherein R² is as defined in any of Embodiments E1-E7, ring A is defined in any of embodiments E8-E11, -L- is as defined in any of Embodiments E12-E18, ring B is as defined in any of Embodiments E19-E32, and R³ and R⁴, together with the carbon to which they are attached, join to form a 5-membered spirocyclic cycloalkyl, and all other variables are as defined in Embodiment E1.

A fifty-first embodiment of the methods of the invention (Embodiment E51) comprises administration of a compound of Formula (I), having the structure:

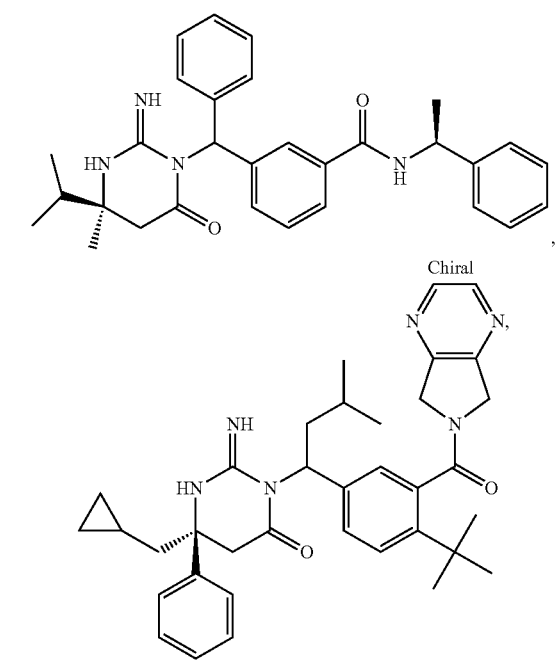

-continued
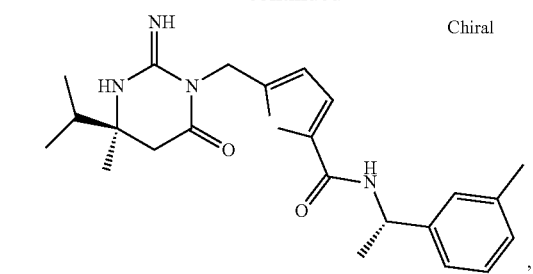
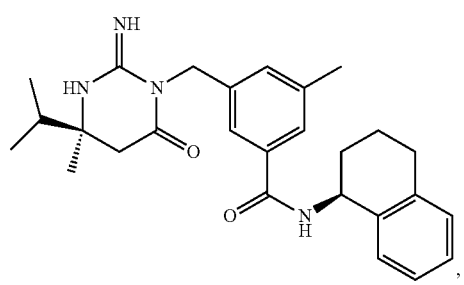
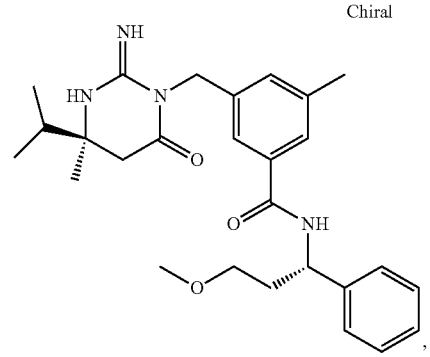
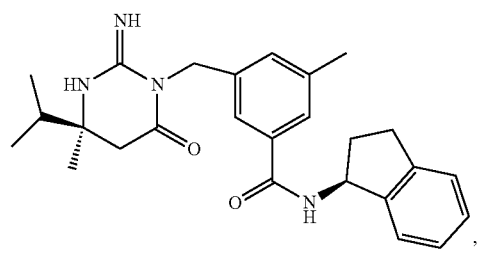
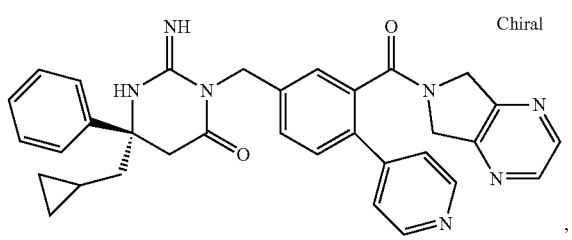
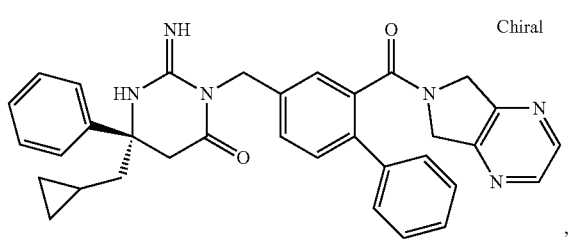
-continued
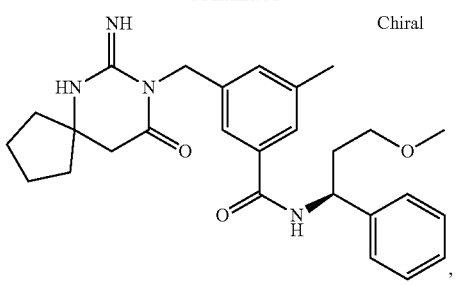
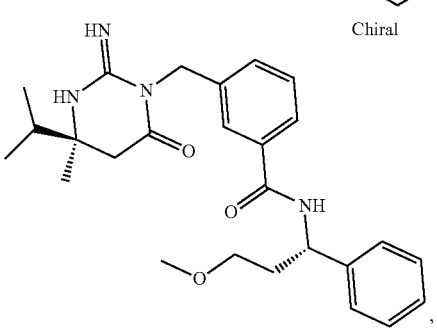
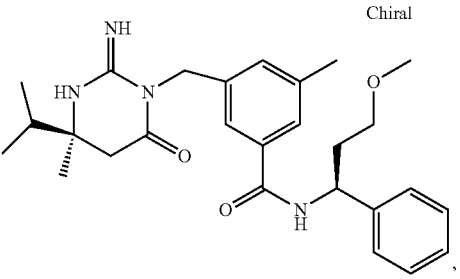
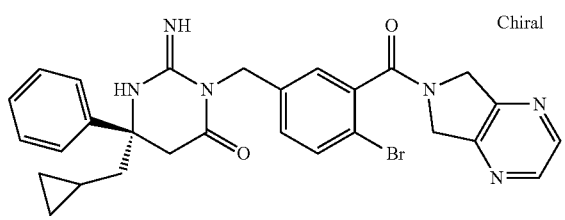
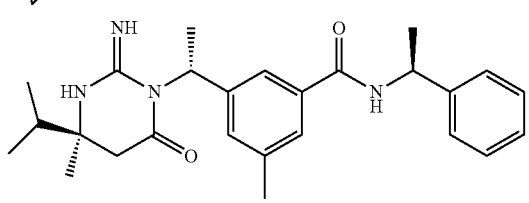
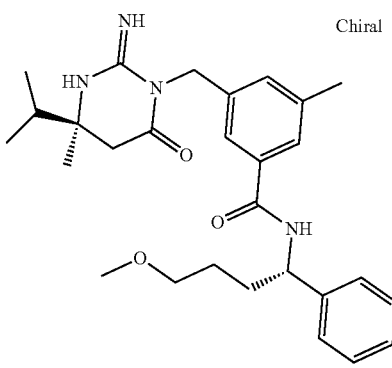

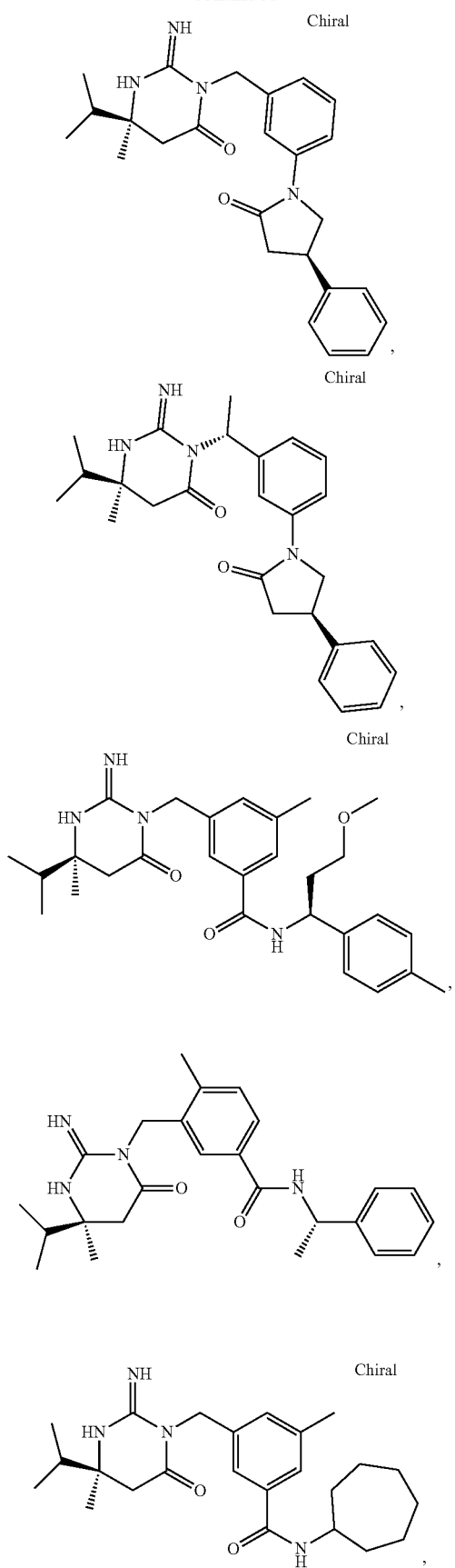
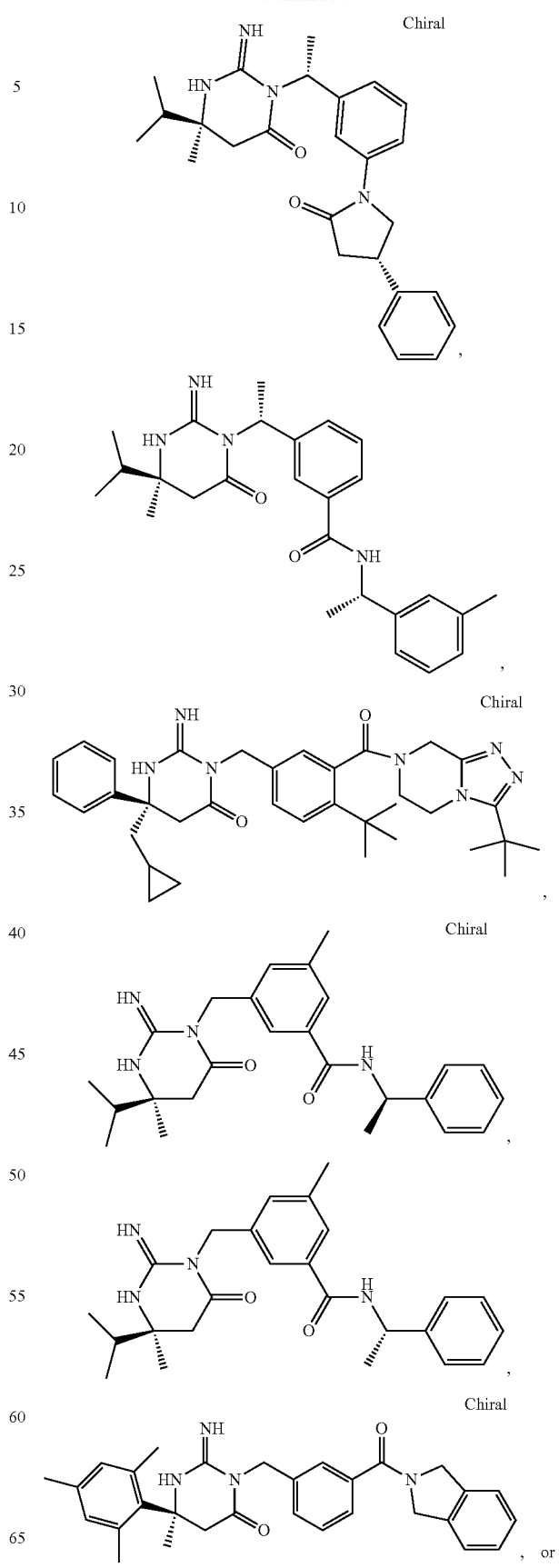

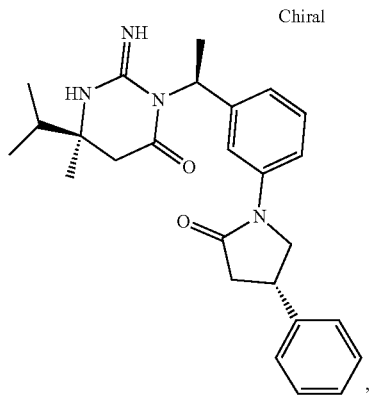

or a pharmaceutically acceptable salt thereof.

A fifty-second embodiment of the methods of the invention (Embodiment E52) comprises administration of a compound as described in Khan et al., WO2013/142396, or a pharmaceutically acceptable salt thereof to a subject in need thereof.

In a further embodiment of the methods of the invention, in the compound of structural Formula (I), or the pharmaceutically acceptable salt thereof:

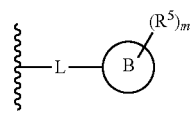

is selected from the group consisting of:

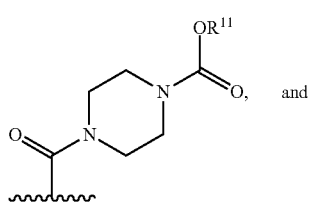

wherein, $R^{11}$ is $C_1$-$C_6$alkyl, optionally substituted with one to three halo or $C_3$-$C_6$cycloalkyl, optionally substituted with one to three halo.

In another embodiment of the methods of the invention, the compound, or the pharmaceutically acceptable salt thereof, has the structural Formula (IA):

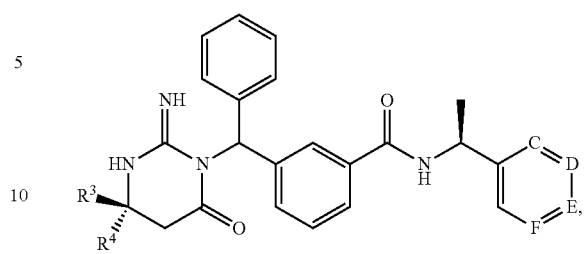

wherein C, D, E, and F, are independently selected from CH and N.

In a further embodiment of the methods of the invention, the compound, or the pharmaceutically acceptable salt thereof, has the structural Formula (IB):

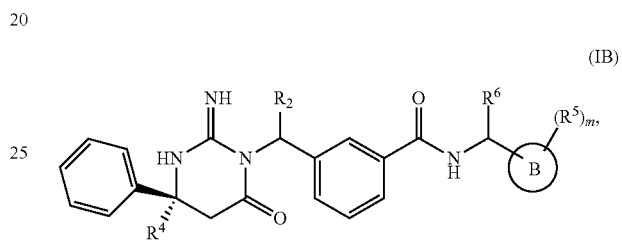

wherein $R^6$ is selected from H, —($C_1$-$C_6$)alkyl and —($C_1$-$C_6$)heteroalkyl.

In another embodiment of the methods of the invention, the compound, or the pharmaceutically acceptable salt thereof, has the structural Formula (IC):

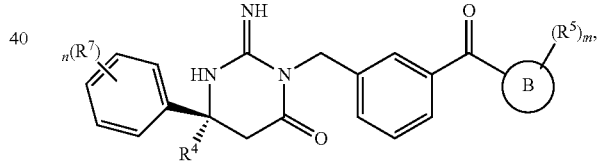

wherein each occurrence of $R^7$ is independently selected from H and halo.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I).

In the various embodiments described herein, each variable is selected independently of the others unless otherwise indicated.

"Drug resistant" means, in connection with a *Plasmodium* parasite strain, a *Plasmodium* species which is no longer susceptible to at least one previously effective drug; which has developed the ability to withstand attack by at least one previously effective drug. A drug resistant strain may relay that ability to withstand to its progeny. Said resistance may be due to random genetic mutations in the bacterial cell that alters its sensitivity to a single drug or to different drugs.

"Patient" includes both human and non-human animals. Non-human animals include those research animals and companion animals such as mice, rats, primates, monkeys, chimpanzees, great apes, dogs, and house cats.

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, and one or more pharmaceutically acceptable carriers or diluents. The term "pharmaceutical composition" is also intended to encompass both the bulk composition and individual dosage units comprised of one or more (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" and "halo" mean fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, —NH—, and —N(alkyl)-. Non-limiting examples include ethers, thioethers, amines, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, hetercycloalkyl, etc. indicates a divalent moiety, e.g., —CH$_2$CH$_2$— is ethylene, and

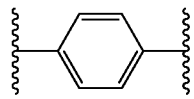 [SMILES: *c1ccc(*)cc1]

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen atom from an alkenyl group that is defined above. Non-limiting examples of alkenylene include —CH=CH—, —C(CH$_3$)=CH—, and —CH=CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moities include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

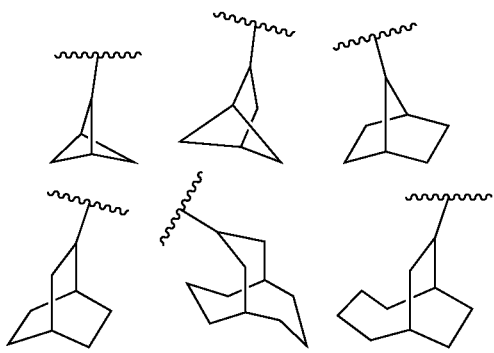

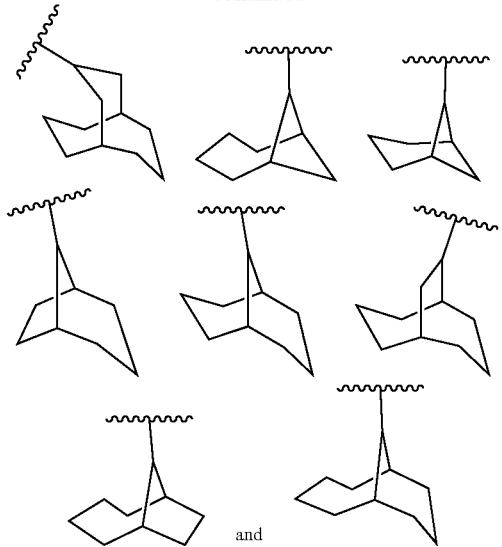

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more substituents, which may be the same or different, as described herein. The term "monocyclic cycloalkenyl" refers to monocyclic versions of cycloalkenyl groups described herein and includes non-aromatic 3- to 7-membered monocyclic cycloalkyl groups which contains one or more carbon-carbon double bonds. Non-limiting examples include cyclopropenyl, cyclobutenyl, cyclopentenyl, cyclohexenyl, cyclohetpenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone)

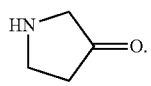

As used herein, the term "monocyclic heterocycloalkyl" refers monocyclic versions of the heterocycloalkyl moities described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

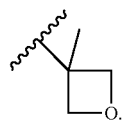

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more substituents, which may be the same or different, as described herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

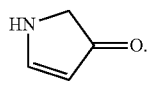

As used herein, the term "monocyclic heterocycloalkenyl" refers to monocyclic versions of the heterocycloalkenyl moities described herein and include 4- to 7-membered monocyclic heterocycloalkenyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof.

It should be noted that in heteroatom-containing ring systems of this invention, there are no hydroxyl groups on carbon atoms adjacent to a N, O or S, as well as there are no N or S groups on carbon adjacent to another heteroatom. For example, in

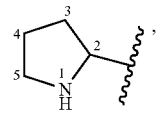

there is no —OH attached directly to carbons marked 2 and 5.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

When a variable appears more than once in a group, e.g., $R^8$ in —N($R^8$)$_2$, or a variable appears more than once in a structure presented herein, the variables can be the same or different.

A solid line —, as a bond generally indicates a mixture of, or either of, the possible isomers, e.g., containing (R)- and (S)-stereochemistry. For example:

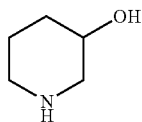

means containing either one of or both

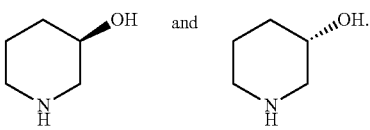

The wavy line ~~~, as used herein shown crossing a line representing a chemical bond, indicates a point of attachment to the rest of the compound. Lines drawn into the ring systems, such as, for example

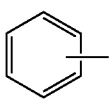

indicates that the indicated line (bond) may be attached to any of the substitutable ring atoms.

"Oxo" is defined as a oxygen atom that is double bonded to a ring carbon in a cycloalkyl, cycloalkenyl, heterocycloalkyl, heterocycloalkenyl, or other ring described herein, e.g.,

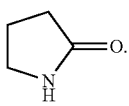

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

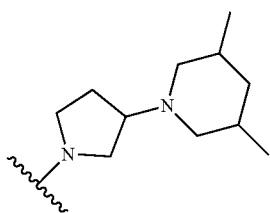 [SMILES: *N1CCC(N2CC(C)CC(C)C2)C1]

represents

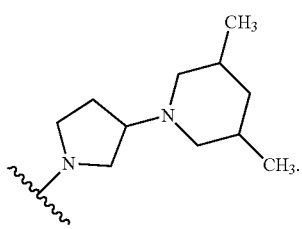 [SMILES: *N1CCC(N2CC(C)CC(C)C2)C1]

In another embodiment, the compounds useful in the methods of the invention, and/or compositions comprising them useful in said methods, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

It shall be understood that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Another embodiment provides prodrugs and/or solvates of the compounds of the invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound useful in the methods of the invention or a pharmaceutically acceptable salt thereof, contains a carboxylic acid functional group, a prodrug can comprise an ester formed by the replacement of the hydrogen atom of the acid group with a group such as, for example, ($C_1$-$C_5$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylamino-ethyl), carbamoyl-($C_1$-$C_2$)alkyl, N,N-di ($C_1$-$C_2$)alkylcarbamoyl-(C1-C2)alkyl and piperidino-, pyrrolidino- or morpholino($C_2$-$C_3$)alkyl, and the like.

Similarly, if a compound used in the methods of the invention contains an alcohol functional group, a prodrug can be formed by the replacement of the hydrogen atom of the alcohol group with a group such as, for example, $(C_1$-$C_6)$alkanoyloxymethyl, 1-(($C_1$-$C_6$)alkanoyloxy)ethyl, 1-methyl-1-(($C_1$-$C_6$)alkanoyloxy)ethyl, $(C_1$-$C_6)$alkoxycarbonyloxymethyl, N—$(C_1$-$C_6)$alkoxycarbonylaminomethyl, succinoyl, $(C_1$-$C_6)$alkanoyl, α-amino$(C_1$-$C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)$alkyl$)_2$ or glycosyl (the radical resulting from the removal of a hydroxyl group of the hemiacetal form of a carbohydrate), and the like.

If a compound used in the methods of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1$-$C_{10})$alkyl, $(C_3$-$C_7)$ cycloalkyl, benzyl, or R-carbonyl is a natural α-aminoacyl or natural α-aminoacyl, —C(OH)C(O)OY$^1$ wherein Y$^1$ is H, $(C_1$-$C_6)$alkyl or benzyl, —C(OY$^2$)Y$^3$ wherein Y$^2$ is $(C_1$-$C_4)$ alkyl and Y$^3$ is $(C_1$-$C_6)$ alkyl, carboxy $(C_1$-$C_6)$alkyl, amino$(C_1$-$C_4)$alkyl or mono-N— or di-N,N—$(C_1$-$C_6)$alkylaminoalkyl, —C(Y$^4$)Y$^5$ wherein Y$^4$ is H or methyl and Y$^5$ is mono-N— or di-N, N—$(C_1$-$C_6)$alkylamino morpholino, piperidin-1-yl or pyrrolidin-1-yl, and the like.

One or more compounds used in the methods of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds used in the methods of the invention may optionally be converted to a solvate. Preparation of solvates is generally known. Thus, for example M. Caira et al, *J. Pharmaceutical Sci.*, 1993, 3, 601-611, describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition used in the methods of the present invention effective in inhibiting the above-noted diseases or enzyme activity and thus producing the desired therapeutic, ameliorative, inhibitory or preventative effect.

Another embodiment provides pharmaceutically acceptable salts of the compounds to be used in the methods of the invention. Thus, reference to a compound used in the methods of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds used in the methods of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quartemized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Another embodiment provides pharmaceutically acceptable esters of the compounds used in the methods of the invention. Such esters include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, another embodiment provides tautomers of the compounds of the invention to be used in the methods herein, and salts, solvates, esters and prodrugs of said tautomers. It shall be understood that all tautomeric forms of such compounds are within the scope of the compounds used in the methods of the invention. For example, all keto-enol and imine-enamine forms of the compounds, when present, are included in the invention.

The compounds used in the methods of the invention may contain asymmetric or chiral centers, and, therefore, exist in different stereoisomeric forms. It is intended that all stereoisomeric forms of the compounds used in the methods of the invention as well as mixtures thereof, including racemic mixtures, form part of the present invention. In addition, the present invention embraces use of all geometric and positional isomers. For example, if a compound used in the methods of the invention incorporates a double bond or a fused ring, both the cis- and trans-forms, as well as mixtures, are embraced within the scope of the invention.

Another embodiment provides for diastereomeric mixtures and individual enantiomers of the compounds used in the methods of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds used in the methods of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds used in the methods of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the methods of the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment provides isotopically-labelled compounds to be used in the methods the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of the invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent.

In the compounds used in the methods of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). The presence of deuterium in the compounds of the invention is indicated by "D". Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds used in the methods of the invention, and of the salts, solvates, esters and prodrugs of the compounds of the invention, are intended to be included in the present invention.

Another embodiment provides suitable dosages and dosage forms of the compounds used in the methods of the invention. Suitable doses for administering compounds used in the methods of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/ day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, in specific embodiments from about 1 mg to about 50 mg, in specific embodiments from about 1 mg to about 25 mg, according to the particular application. In another embodiment, a typical recommended daily dosage regimen for oral administration can range from about 1 mg/day to about 500 mg/day, in specific embodiments 1 mg/day to 200 mg/day, in two to four divided doses.

As discussed above, the amount and frequency of administration of the compounds of the invention and/or the pharmaceutically acceptable salts thereof will be regulated according to the judgment of the attending clinician considering such factors as age, condition and size of the patient as well as severity of the symptoms being treated.

When used in combination with one or more additional therapeutic agents ("combination therapy"), the compounds used in the methods of this invention, i.e. the compounds of Formula (I), (A), (IB) or (IC), may be administered together or sequentially. When administered sequentially, compounds of the invention may be administered before or after the one or more additional therapeutic agents, as determined by those skilled in the art or patient preference.

If formulated as a fixed dose, such combination products employ the compounds of Formula (I), (A), (IB) or (IC) within the dosage range described herein and the other pharmaceutically active agent or treatment within its dosage range.

Accordingly, another embodiment provides methods for the treatment of malaria or for the treatment of *Plasmodium* infection, comprising administration of combinations comprising an amount of at least one compound of Formula (I), (A), (IB) or (IC), or a pharmaceutically acceptable salt, solvate, ester or prodrug thereof, and an effective amount of one or more additional agents described below. The pharmacological properties of the compounds of Formula (I), (A), (IB) or (IC) may be confirmed by a number of pharmacological assays. Certain assays are exemplified herein.

Another embodiment provides for methods of treatment using pharmaceutically acceptable compositions comprising a compound of the invention, either as the neat chemical or optionally further comprising additional ingredients. Such compositions are contemplated for preparation and use alone or in combination therapy. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Non-limiting examples of additional drugs and active agents useful in combination therapies for the treatment of malaria, include the following: Coartem® (Novartis International AG, Basel, Switzerland; artemether+lumefantrine), Eurartesim® (Sigma-Tau Pharmaceuticals, Inc., Rome, Italy; dihydroartemisinin-piperaquine), Pyramax® (Shin Poong Pharmaceutical Co., Ltd., Seoul, Korea; pyronaridine-artesunate), ASAQ Winthrop® (Sanofi SA (Gentilly, France)/DNDi (Geneva, Switzerland); artesunate+amodiaquine), ASMQ (Cipla Limited (Mumbai, India)/DNDi, artesunate+mefloquine), SPAQ-CO™ (Guilin Pharmaceutical Co., Ltd. (Shanghai), amodiaquine+sulfadoxine, pyrimethamine), Artesun® (Guilin Pharmaceutical, artesunate), artemether, artesunate, dihydroartemisinin, lumefantrine, amodiaquine, mefloquine, piperaquine, quinine, chloroquine, atovaquone and proguanil and sulfadoxine-pyrimethamine, Tafenoquine (Glaxosmithkline), OZ439/PQP (Sanofi), OZ439/FQ (Sanofi), KAE609 (Novartis), KAF156 (Novartis), DSM265 (NIH/Takeda), and MK-4815 (Merck & Co., Inc., Powles et al., *Antimicrobial Agents and Chemotherapy* 56(5): 2414-2419(2012)). Selection of such additional active ingredients will be according to the diseases or disorders present for which treatment is desired, as determined by the attending physician or other health care provider.

Thus, the invention also provides methods of using the compounds of Formula (I), (IA), (IB), or (IC) to inhibit plasmepsin V, to treat *Plasmodium* infection or treat malaria wherein the method further comprises administering to a subject in need thereof, one or more additionl anti-malarial agents. In some embodiments, the one or more additional anti-malarial agents are selected from the group consisting of: artemether, lumefantrine, dihydroartemisinin, piperaquine, pyronaridine, artesunate, amodiaquine, mefloquine, sulfadoxine, pyrimethamine, lumefantrine, quinine, chloroquine, atovaquone, and proguanil.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment provides for use of compositions comprising a compound of Formula (I), (A), (IB) or (IC) formulated for transdermal delivery. The transdermal compositions can take the form of creams, lotions, aerosols and/or emulsions and can be included in a transdermal patch of the matrix or reservoir type as are conventional in the art for this purpose.

Another embodiment provides for use of compositions comprising a compound of Formula (I), (A), (IB) or (IC) formulated for subcutaneous delivery. Another embodiment provides for use of compositions suitable for oral delivery. In some embodiments, it may be advantageous for the pharmaceutical preparation comprising one or more compounds of Formula (I), (A), (IB) or (IC) to be prepared in a unit dosage form. In such forms, the preparation is subdivided into suitably sized unit doses containing appropriate quantities of the active component, e.g., an effective amount to achieve the desired purpose. Each of the foregoing alternatives is considered as included in the various embodiments of the invention.

Abbreviations employed herein include the following:
- 1-(3-Dimethylaminopropyl)-3-ethylcarbodiimide hydrochloride: EDCI
- Chlorotitanium triisopropoxide: ClTi(iOPr)$_3$
- Diatomaceous earth: CELITE
- Diisopropyl azodicarboxylate: DIAD
- Dichloromethane: DCM
- Diisopropylethylamine: DIPEA
- 4-(Dimethylamino)pyridine: DMAP
- Dimethylformamide: DMF
- Ether or diethyl ether: Et$_2$O
- Ethyl: Et
- Ethyl acetate: EtOAc or EA
- Ethyl alcohol: EtOH
- Example: Ex.
- Hours: hrs or h
- 1-Hydroxybenzotriazole: HOBt or HOBT
- Lithium diisopropylamide: LDA
- Methanol: MeOH
- Minutes: min
- N-t-Butoxycarbonylamide: BocNH$_2$
- Palladium(II) hydroxide: Pd(OH)$_2$
- Petroleum ether: PE
- Preparative high performance liquid chromatography: Prep-HPLC
- Room temperature (ambient, ~25° C.): rt or RT
- Supercritical fluid chromatography: SFC
- tert-Butoxycarbonyl: t-Boc or Boc
- tert-Butoxycarbonyl anhydride Boc$_2$O
- Tetrahydrofuran: THF
- Triethylamine: Et$_3$N
- Trifluoroacetic acid: TFA
- Trifluroacetic anhydride: TFAA

EXAMPLES

In general, the compounds used in the methods of the invention, i.e. compounds of Formula (I), (A), (IB) or (IC), may be produced by a variety of processes known to those skilled in the art and by known processes analogous thereto. The invention disclosed herein is exemplified by the following preparations which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatibility.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme and in the preparations and examples described below.

The invention disclosed herein is exemplified by the following illustrative processes which should not be construed to limit the scope of the disclosure. Alternative mechanistic pathways and analogous structures will be apparent to those skilled in the art.

Method A:

Method A is a general method for compounds of Formula (I) that relies on the formation of intermediate A8. In this method, a ketone represented by structure A1 is condensed with a sulfoxamine such as A2 to provide an imine A3. This imine A3 is subsequently reacted with an appropriate ester A4 under basic conditions to give intermediate A5 according to the procedures of Ellman et al. (*Acc. Chem. Res.* 35 (11): 984-995 (2002)). Deprotection under acidic conditions to give amino ester A6 and coupling with a protected isothiocyanate (shown here for example using 2,4 dimethoxybenzyl isothiocyanate I-3) affords an iminopyrimidinone A7. Removal of the protecting group under hydrogenolysis conditions gives intermediate A8. Condensation of A8 with alcohols such as A9 provides compounds of type A10 which can be further reacted under acidic conditions to provide the compound of Formula (I).

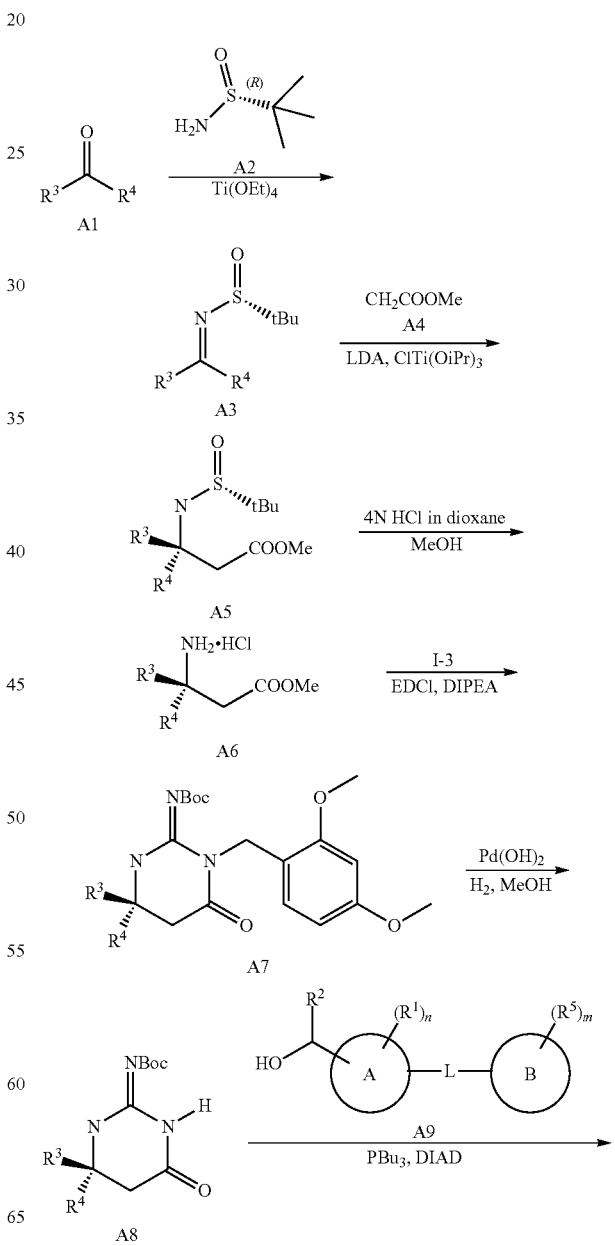

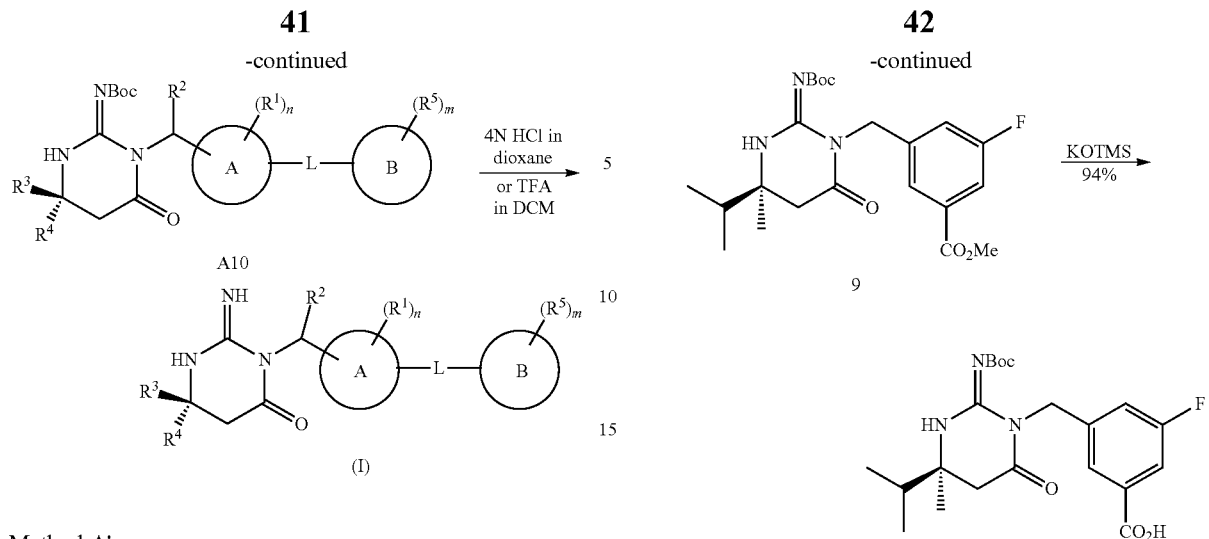

Method A'

A modification of this route provided a convergent synthesis as shown here:

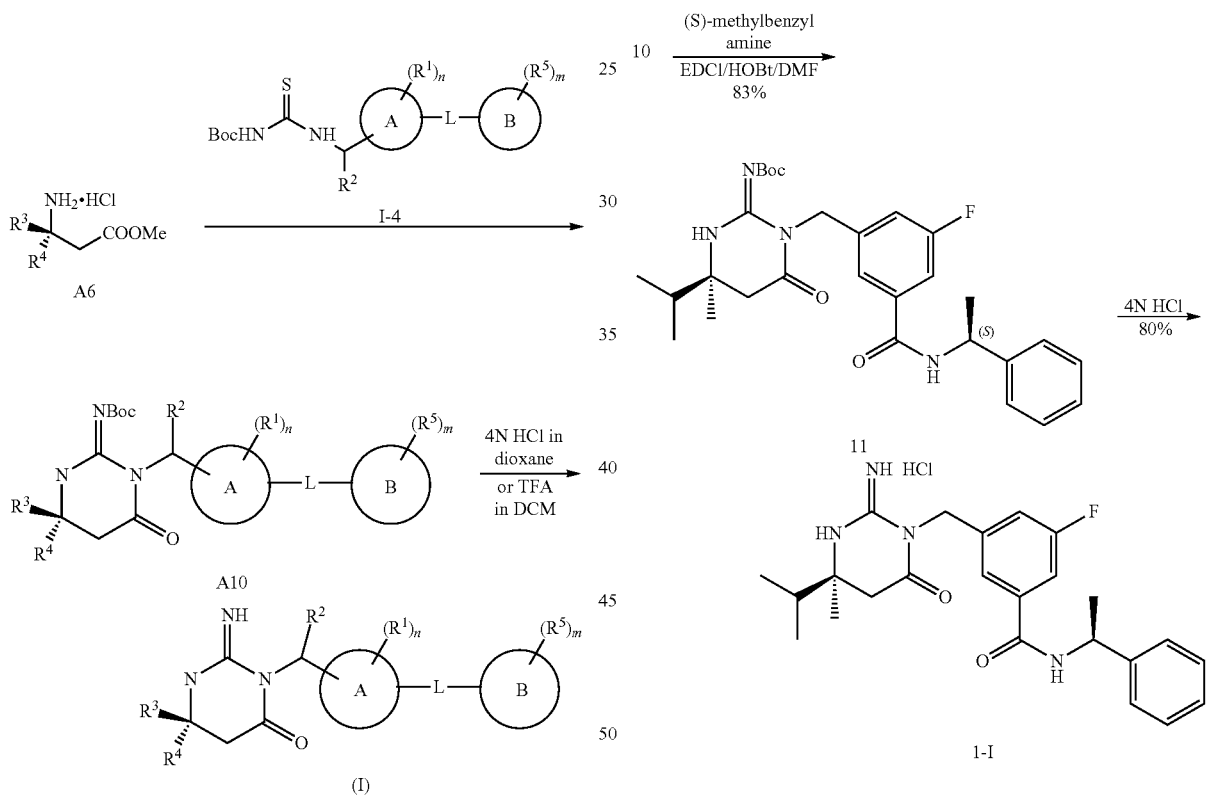

Compounds A6 are condensed with the Boc-protected thioureas I-4 using a reagent such as a carbodiimide to provide the compounds A10 which are elaborated into compounds of Formula I as in method A.

A representative example that was prepared according to Method A' is illustrated below:

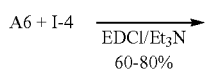

Intermediates A6 and I-4 are reacted with a coupling reagent such as EDCI with triethylamine in DMF to give the ester 9. This is converted to the acid using potassium trimethylsilanolate (TMSOK) to give 10 which is condensed with (S)-methylbenzyl amine using a carbodiimide peptide coupling reagent such as EDCI with HOBT in DMF. The amide 11 is then treated with HCl in dioxane to provide example 1-I.

Method B:

Method B is a general alternate method for compounds of Formula (I) that relies on using compounds such as B9 (in place of A9) wherein the ring A contains a functional group (such as Cl, Br, I, or CN) to provide compounds B10. The functional group ("FG") is then converted into the -L-phenyl-$(R^5)_m$ (or alternative -L-ring B—$(R^5)_m$) substitutent and then subsequently deprotected to provide compounds of formula I.

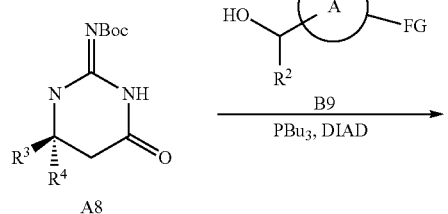

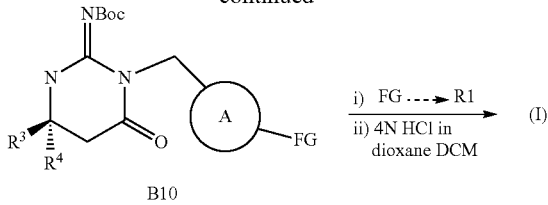

Specific compounds useful in the methods of the invention were synthesized using generally the same procedures as described in Khan et al., WO 2013/142396, substituting the appropriate reactants and reagents.

Compounds 27-56 were made via the following methods, substituting the appropriate reactants and reagents.

Method C

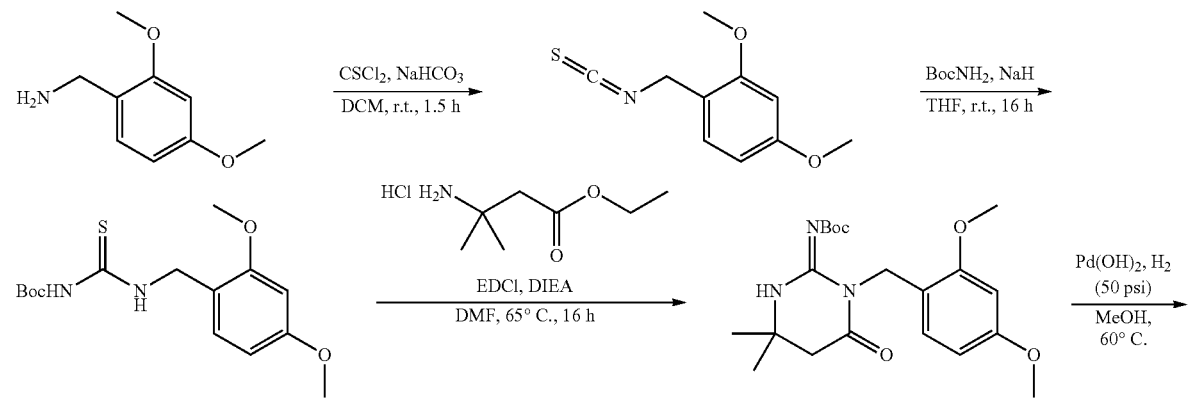

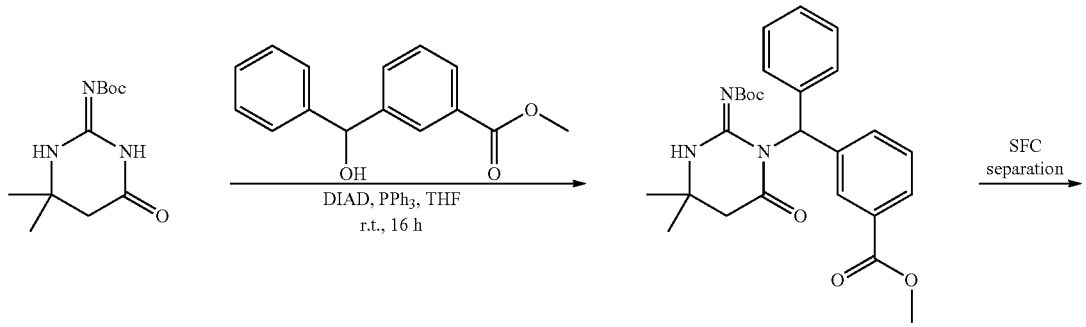

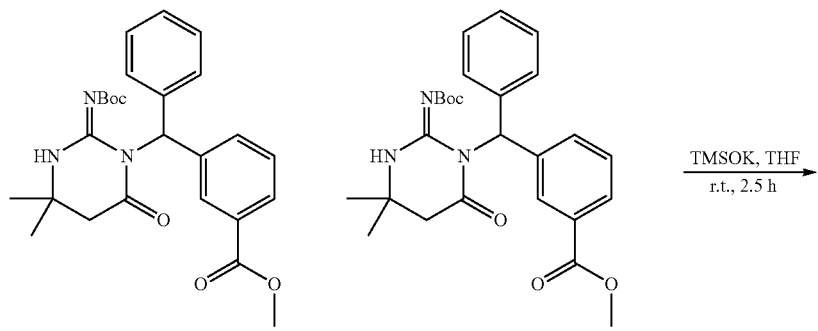

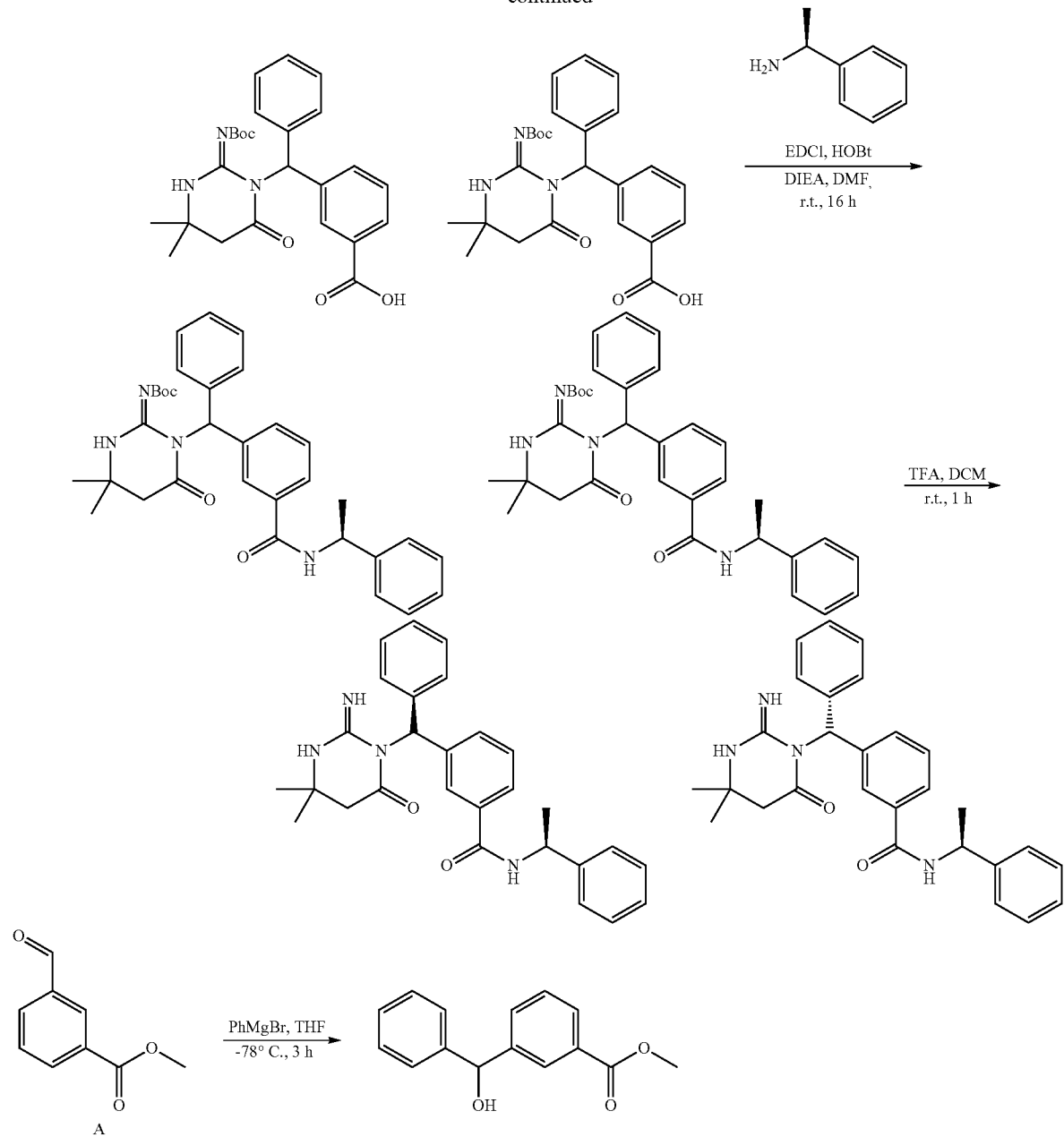

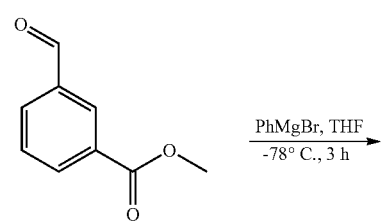

Step 1: Methyl 3-(hydroxy(phenyl)methyl)benzoate

Phenylmagnesium bromide (30.5 mL, 91 mmol) was added dropwise to a solution of methyl 3-formylbenzoate (10 g, 60.9 mmol) in THF (100 mL) at −78° C. under $N_2$ atmosphere. Then the mixture was stirred at −78° C. for 3 h. The mixture was quenched with saturated aqueous $NH_4Cl$ (50 mL), and extracted with ethyl acetate (50 mL×3). The combined organic layers were washed with brine (50 mL), dried over $Na_2SO_4$, filtered and concentrated in vacuo. The residue was purified by flash column chromatography (SiO$_2$, PE:EA=20:1 to 5:1) to afford methyl 3-(hydroxy(phenyl)methyl)benzoate. HNMR (400 MHz, CDCl$_3$): δ 8.10 (s, 1H), 7.94-7.95 (m, 1H), 7.58-7.60 (m, 1H), 7.28-7.44 (m, 6H), 5.90 (s, 1H), 3.91 (s, 3H), 2.31 (s, 1H). MS (ESI) m/z 225.0 (M+H-18)$^+$.

Step 2: 1-(isothiocyanatomethyl)-2,4-dimethoxybenzene

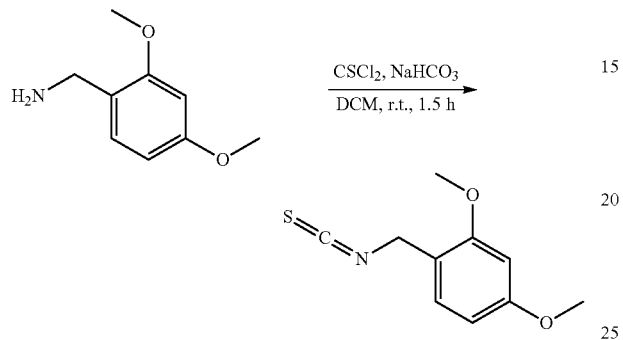

Saturated NaHCO$_3$ (100 mL) was added to a solution of (2,4-dimethoxyphenyl)methanamine (10 mL, 66.4 mmol) in CH$_2$Cl$_2$ (100 mL) and the mixture was stirred vigorously at 25° C. for 15 min. Then thiophosgene (10 mL, 131 mmol) was added via syringe to the bottom layer. The mixture was stirred at 25° C. for 1.5 h. The aqueous layer was separated and the organic layer was washed with brine (100 mL), dried over NaSO$_4$, filtered, and concentrated in vacuo to afford 1-(isothiocyanatomethyl)-2,4-dimethoxybenzene. HNMR (400 MHz, CDCl$_3$): δ 7.19 (d, J=7.6 Hz, 1H), 6.47-6.50 (m, 2H), 4.61 (s, 2H), 3.84 (s, 3H), 3.82 (s, 3H).

Step 3: 1-(2,4-dimethoxybenzyl)-3-Boc-thiourea

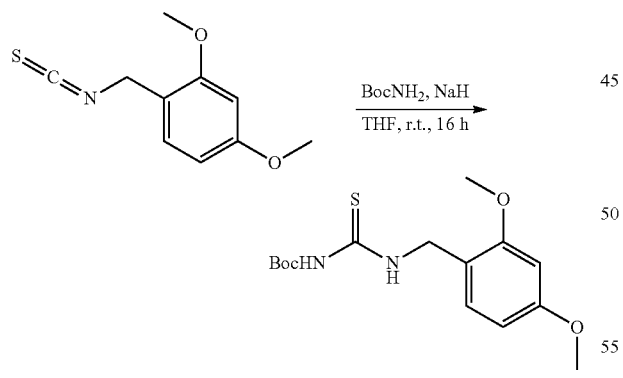

Sodium hydride (5.31 g, 133 mmol) was added to a solution of tert-butyl carbamate (11.66 g, 100 mmol) in THF (150 mL) at 0° C. and the mixture was stirred for 15 min. 1-(isothiocyanatomethyl)-2,4-dimethoxybenzene (13.89 g, 66.4 mmol) in THF (50 mL) was added dropwise at 0° C. The mixture was warmed to room temperature and stirred at 25° C. for 16 h. The mixture was quenched with water (50 mL), extracted with ethyl acetate (100 mL×3). The combined organic layers were washed with brine (150 mL), dried over Na$_2$SO$_4$, filtered and concentrated in vacuo. The crude was purified by flash column chromatography (SiO$_2$, PE:EA=20:1 to 5:1) to afford 1-(2,4-dimethoxybenzyl)-3-Boc-thiourea. HNMR (400 MHz, CDCl$_3$): δ 10.05 (brs, 1H), 7.79 (brs, 1H), 7.28 (d, J=8.8 Hz, 1H), 6.44-6.48 (m, 2H), 4.79 (d, J=5.6 Hz, 2H), 3.85 (s, 3H), 3.81 (s, 3H), 1.46 (s, 9H). MS (ESI) m/z 327 [M+H]$^+$.

Step 4: tert-butyl (1-(2,4-dimethoxybenzyl)-4,4-dimethyl-6-oxotetrahydropyrimidin-2(1H)-ylidene)carbamate

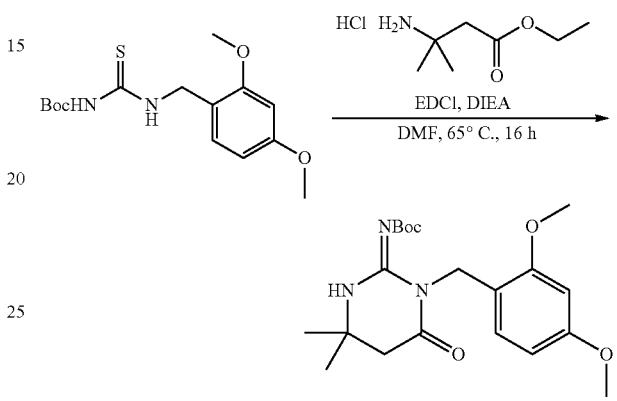

N,N-Diisopropylethylamine (DIEA) (8.03 mL, 46.0 mmol), EDCI (5.29 g, 27.6 mmol) and 1-(2,4-dimethoxybenzyl)-3-Boc-thiourea (3 g, 9.19 mmol) were added to a solution of ethyl 3-amino-3-methylbutanoate hydrochloride (1.670 g, 9.19 mmol) in DMF (100 mL). The reaction was stirred at 65° C. for 16 h. The mixture was quenched with water (40 mL), and extracted with ethyl acetate (40 mL×3). The organic layers were washed with brine (40 mL), dried over Na$_2$SO$_4$, filtered, and concentrated in vacuo. The crude was purified by flash column chromatography (SiO$_2$, PE:EA=50:0 to 10:1) to afford tert-butyl (1-(2,4-dimethoxybenzyl)-4,4-dimethyl-6-oxotetrahydropyrimidin-2(1H)-ylidene)carbamate. HNMR (400 MHz, CDCl$_3$): δ 9.81 (br, 1H), 7.11 (d, J=8.8 Hz, 1H), 6.39-6.43 (m, 2H), 5.11 (s, 2H), 3.79 (s, 3H), 3.78 (s, 3H), 2.60 (s, 2H), 1.49 (s, 9H), 1.33 (s, 6H). MS (ESI) m/z 392 [M+H]$^+$.

Step 5: tert-butyl (4,4-dimethyl-6-oxotetrahydropyrimidin-2(1H)-ylidene)carbamate

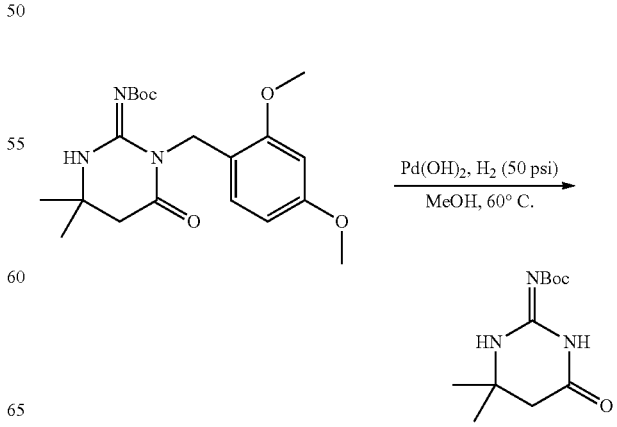

Pd(OH)₂ (0.430 g, 3.07 mmol) was added to a solution of tert-butyl (1-(2,4-dimethoxybenzyl)-4,4-dimethyl-6-oxotetrahydropyrimidin-2(1H)-ylidene)carbamate (2.0 g, 5.11 mmol) in MeOH (30 mL). The mixture was stirred at 60° C. for 2 days under H₂ (50 psi) atmosphere. Then the mixture was filtered through a pad of CELITE. The filtrate was concentrated in vacuo. The crude was purified by flash column chromatography (SiO₂, PE:EA=100:0 to 1:1) to give tert-butyl (4,4-dimethyl-6-oxotetrahydropyrimidin-2(1H)-ylidene)carbamate. HNMR (400 MHz, CDCl₃): δ 2.58 (s, 2H), 1.50 (s, 9H), 1.41 (s, 6H). MS (ESI) m/z 242 [M+H]⁺.

Step 6: methyl 3-((2-((tert-butoxycarbonyl)imino)-4,4-dimethyl-6-oxotetrahydropyrimidin-1(2H)-yl)(phenyl)methyl)benzoate

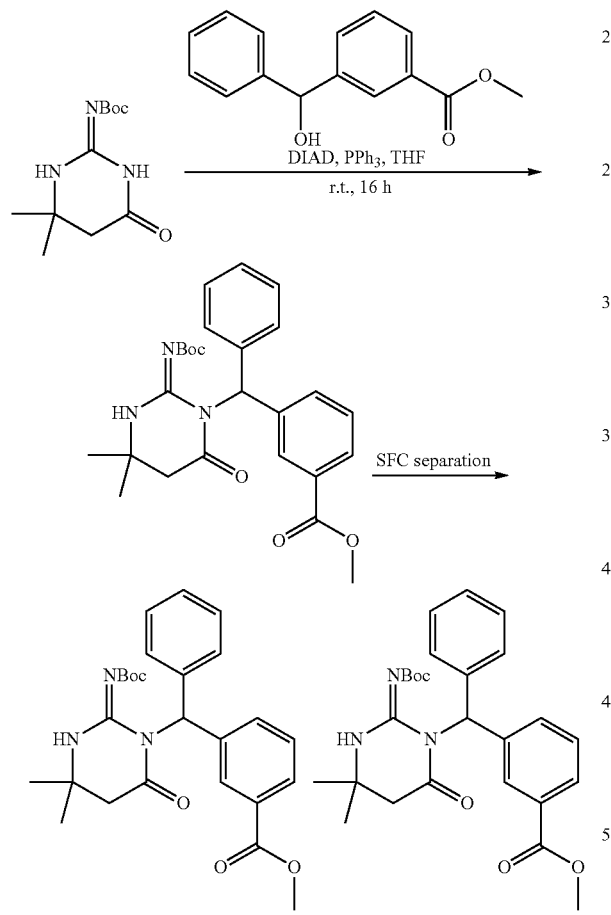

DIAD (0.817 mL, 4.14 mmol) dropwise was added to a solution of tert-butyl (4,4-dimethyl-6-oxotetrahydropyrimidin-2(1H)-ylidene)carbamate (500 mg, 2.072 mmol), methyl 3-(hydroxy(phenyl)methyl)benzoate (602 mg, 2.487 mmol) and PPh₃ (815 mg, 3.11 mmol) in THF (5 mL) at 0° C. under N2 atmosphere. Then the mixture was stirred at 20° C. for 16 h. The mixture was diluted with water (10 mL), and extracted with ethyl acetate (10 mL×3). The combined organic layers were washed with brine (10 mL), dried over Na₂SO₄, filtered, concentrated in vacuo. The residue was purified by flash column chromatography (SiO₂, PE:EA=20:0 to 5:1) to afford methyl 3-((2-((tert-butoxycarbonyl)imino)-4,4-dimethyl-6-oxotetrahydropyrimidin-1 (2H)-yl)(phenyl)methyl)benzoate. MS (ESI) m/z 466 [M+H]methyl 3-((2-((tert-butoxycarbonyl)imino)-4,4-dimethyl-6-oxotetrahydropyrimidin-1(2H)-yl)(phenyl)methyl)benzoate (130 mg, 0.279 mmol) was purified by SFC (Method Column OD(250 mm*30 mm, 5 um); Condition 0.1% NH3H2O ETOH; Begin B 30% End B 30%; Gradient Time(min); 100% B Hold Time(min); FlowRate(mL/min) 60; Injections 120) to afford (S)-methyl 3-((2-((tert-butoxycarbonyl)imino)-4,4-dimethyl-6-oxotetrahydropyrimidin-1 (2H)-yl)(phenyl)methyl)benzoate (peak 1, 60 mg, 0.129 mmol) and (R)-methyl 3-((2-((tert-butoxycarbonyl)imino)-4,4-dimethyl-6-oxotetrahydropyrimidin-1(2H)-yl)(phenyl)methyl)benzoate (peak 2, 60 mg, 0.129 mmol). P1 HNMR (400 MHz, CDCl₃): δ 10.00 (s, 1H), 7.99 (s, 1H), 7.92 (d, J=7.6 Hz, 1H), 7.65 (s, 1H), 7.49 (d, J=7.6 Hz, 1H), 7.34-7.39 (m, 3H), 7.29-7.34 (m, 2H), 7.26-7.29 (m, 1H), 3.85-3.89 (m, 3H), 2.53-2.62 (m, 2H), 1.49 (s, 9H), 1.36 (d, J=18.4 Hz, 6H). P2 HNMR (400 MHz, CDCl₃): δ 10.01 (s, 1H), 7.99 (s, 1H), 7.92 (d, J=8.4 Hz, 1H), 7.65 (s, 1H), 7.49 (d, J=6.4 Hz, 1H), 7.34-7.39 (m, 3H), 7.29-7.34 (m, 2H), 7.26-7.29 (m, 1H), 3.82-3.88 (m, 3H), 2.57 (m, 2H), 1.49 (s, 9H), 1.36 (d, J=18.4 Hz, 6H)

Step 7: 3-((2-((tert-butoxycarbonyl)imino)-4,4-dimethyl-6-oxotetrahydropyrimidin-1 (2H)-yl) (phenyl)methyl)benzoic acid

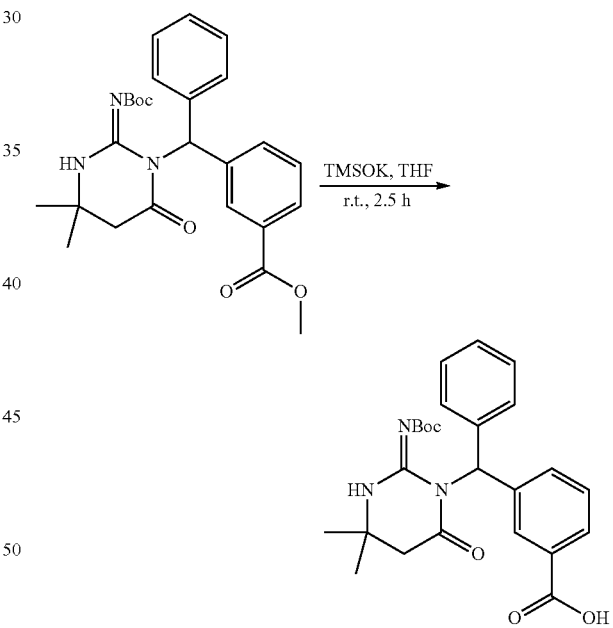

Potassium trimethylsilanolate (33.1 mg, 0.258 mmol) was added to a solution of (S)- and/or (R)-methyl 3-((2-((tert-butoxycarbonyl)imino)-4,4-dimethyl-6-oxotetrahydropyrimidin-1 (2H)-yl)(phenyl)methyl)benzoate (60 mg, 0.129 mmol) in THF (5 mL). The reaction was stirred at 15° C. for 2.5 h. Once finished, the mixture was concentrated in vacuo. Then the crude was taken up in water (10 mL), and neutralized to pH 5-6 with 1M HCl aq., extracted with ethyl acetate (10 mL*3), dried over Na₂SO₄ and concentrated in vacuo to afford (S)- and/or (R)- as applicable 3-((2-((tert-butoxycarbonyl)imino)-4,4-dimethyl-6-oxotetrahydropyrimidin-1(2H)-yl)(phenyl)methyl)benzoic acid. MS (ESI) m/z 452 [M+H]⁺.

Step 8: tert-butyl (4,4-dimethyl-6-oxo-1-(phenyl(3-(((S)-1-phenylethyl) carbamoyl)phenyl)methyl)tetrahydropyrimidin-2(1H)-ylidene)carbamate

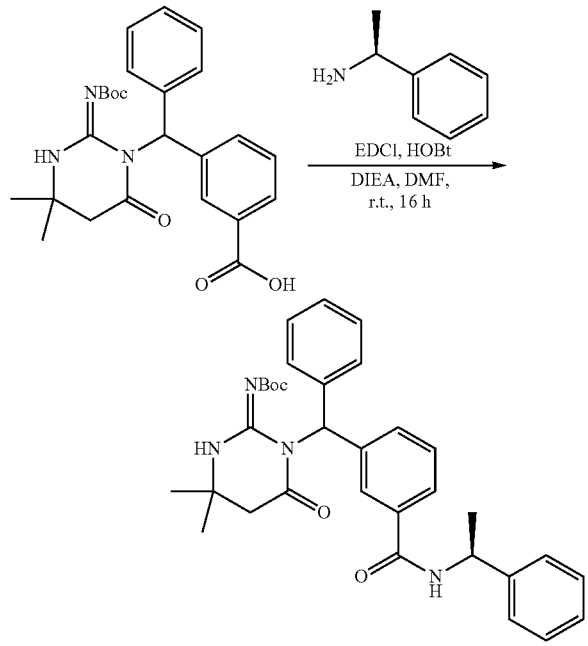

DIEA (0.029 mL, 0.168 mmol) was added to a solution (S)- and/or (R)-3-((2-((tert-butoxycarbonyl)imino)-4,4-dimethyl-6-oxotetrahydropyrimidin-1(2H)-yl)(phenyl)methyl) benzoic acid (19 mg, 0.042 mmol), (S)-1-phenylethanamine (7.65 mg, 0.063 mmol), hydroxybenzotriazole (8.53 mg, 0.063 mmol) and 1-ethyl-3-(3-dimethylaminopropyl)carbodiimide (24.20 mg, 0.126 mmol) in THF (2 mL). The reaction was heated at 15° C. for 16 h. The mixture was quenched with water (10 mL), and extracted with ethyl acetate (15 mL×3). The organic layers were washed with brine (10 mL), dried over $Na_2SO_4$, filtered, and concentrated in vacuo to afford crude (S)- and/or (R)- as applicable tert-butyl (4,4-dimethyl-6-oxo-1-(phenyl(3-(((S)-1-phenylethyl)carbamoyl)phenyl)methyl)tetrahydropyrimidin-2(1H)-ylidene)carbamate. MS (ESI) m/z 555 [M+H]$^+$.

Step 9: 3-((2-imino-4,4-dimethyl-6-oxotetrahydropyrimidin-1(2H)-yl)(phenyl)methyl)-N—((S)-1-phenylethyl)benzamide

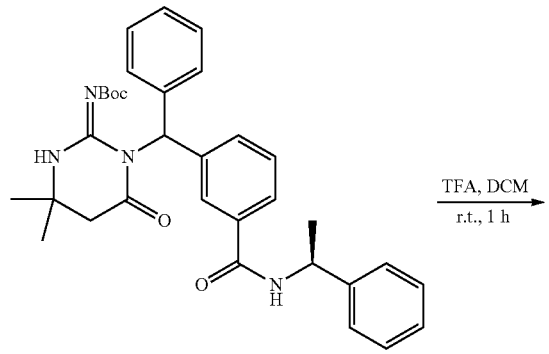

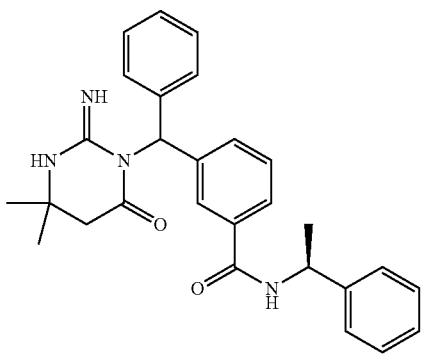

A solution of (S)- and/or (R)-tert-butyl (4,4-dimethyl-6-oxo-1-(phenyl(3-(((S)-1-phenylethyl)carbamoyl)phenyl) methyl)tetrahydropyrimidin-2(1H)-ylidene)carbamate (23 mg, 0.041 mmol) in DCM (2 mL) and TFA (0.5 mL) was stirred at 15° C. for 1 h. The mixture was concentrated in vacuo to give the crude product which was purified by Prep-HPLC (0.1% TFA) to afford (S)- and/or (R)- as applicable 3-((2-imino-4,4-dimethyl-6-oxotetrahydropyrimidin-1(2H)-yl)(phenyl)methyl)-N—((S)-1-phenylethyl)benzamide. EBR1140A_M105_B HNMR (400 MHz, MeOD): δ 7.83-7.89 (m, 1H), 7.79 (s, 1H), 7.48-7.54 (m, 2H), 7.38-7.46 (m, 4H), 7.34-7.38 (m, 3H), 7.29-7.34 (m, 3H), 7.21-7.25 (m, 1H), 7.02 (s, 1H), 5.23 (q, J=7.2 Hz, 1H), 2.92 (d, J=2.4 Hz, 2H), 1.56 (d, J=6.8 Hz, 3H), 1.36 (s, 3H), 1.33 (s, 3H). MS (ESI) m/z 455.3 [M+H]$^+$.

EBR1140A_M105_A HNMR (400 MHz, MeOD): δ 7.85-7.86 (m, 1H), 7.78 (s, 1H), 7.50-7.51 (m, 2H), 7.35-7.43 (m, 9H), 7.32-7.33 (m, 1H), 7.01 (s, 1H), 5.21-5.26 (q, J=7.2 Hz, 2H), 2.87-2.96 (m, 2H), 1.55 (d, J=7.2 Hz, 3H), 1.36 (s, 3H), 1.32 (s, 3H). MS (ESI) m/z 455 [M+H]$^+$.

Method D

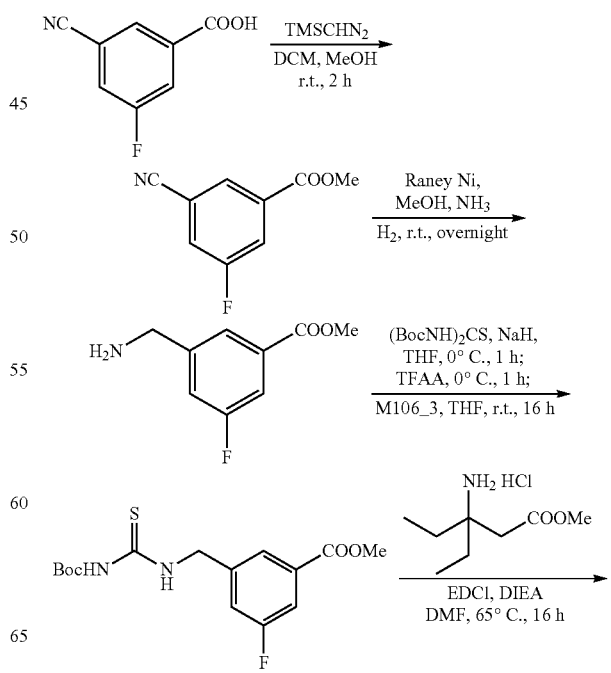

US 11,766,435 B2

53

-continued

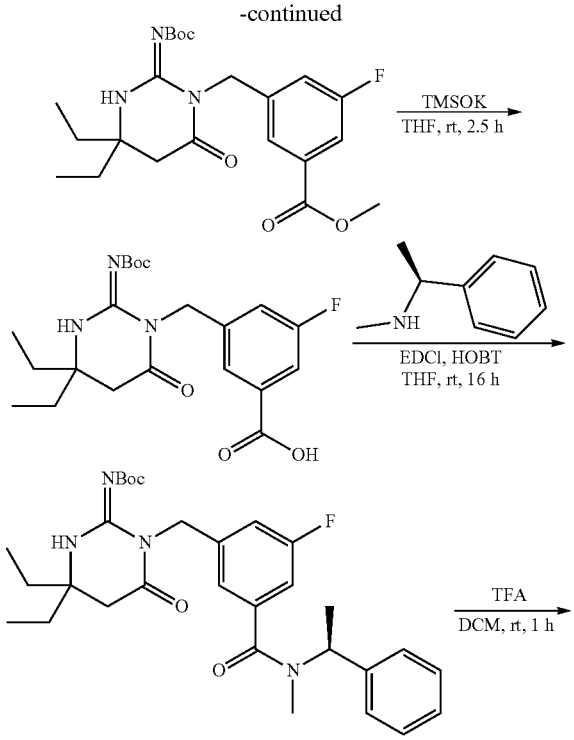

54

Step 1: (R)-2-methyl-N-(pentan-3-ylidene)propane-2-sulfinamide

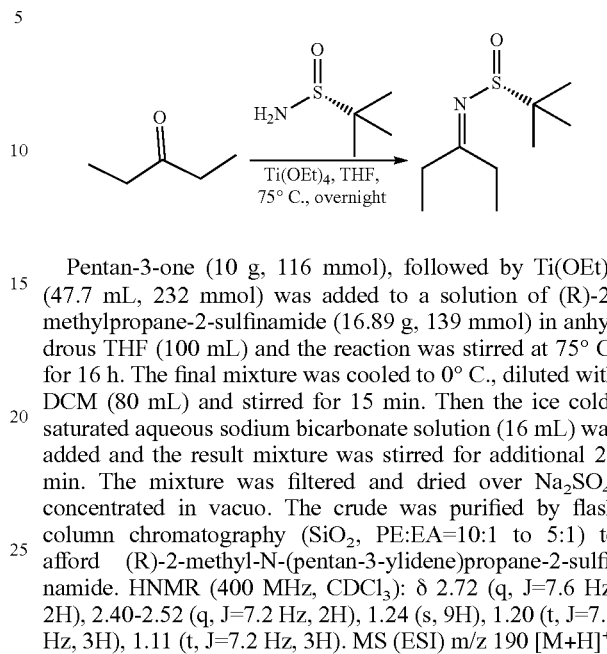

Pentan-3-one (10 g, 116 mmol), followed by Ti(OEt)$_4$ (47.7 mL, 232 mmol) was added to a solution of (R)-2-methylpropane-2-sulfinamide (16.89 g, 139 mmol) in anhydrous THF (100 mL) and the reaction was stirred at 75° C. for 16 h. The final mixture was cooled to 0° C., diluted with DCM (80 mL) and stirred for 15 min. Then the ice cold-saturated aqueous sodium bicarbonate solution (16 mL) was added and the result mixture was stirred for additional 20 min. The mixture was filtered and dried over Na$_2$SO$_4$, concentrated in vacuo. The crude was purified by flash column chromatography (SiO$_2$, PE:EA=10:1 to 5:1) to afford (R)-2-methyl-N-(pentan-3-ylidene)propane-2-sulfinamide. HNMR (400 MHz, CDCl$_3$): δ 2.72 (q, J=7.6 Hz, 2H), 2.40-2.52 (q, J=7.2 Hz, 2H), 1.24 (s, 9H), 1.20 (t, J=7.6 Hz, 3H), 1.11 (t, J=7.2 Hz, 3H). MS (ESI) m/z 190 [M+H]$^+$.

Step 2: (R)-methyl 3-(1,1-dimethylethylsulfinamido)-3-ethylpentanoate

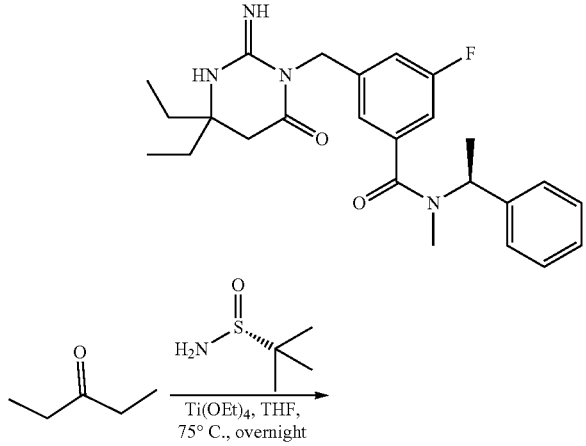

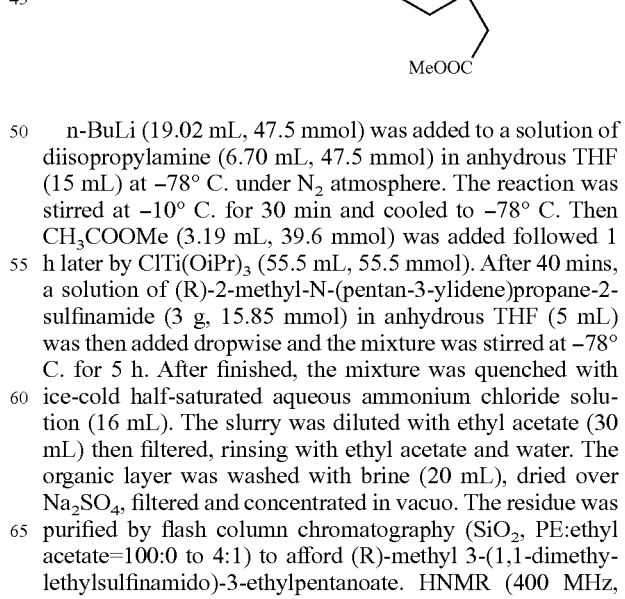

n-BuLi (19.02 mL, 47.5 mmol) was added to a solution of diisopropylamine (6.70 mL, 47.5 mmol) in anhydrous THF (15 mL) at −78° C. under N$_2$ atmosphere. The reaction was stirred at −10° C. for 30 min and cooled to −78° C. Then CH$_3$COOMe (3.19 mL, 39.6 mmol) was added followed 1 h later by ClTi(OiPr)$_3$ (55.5 mL, 55.5 mmol). After 40 mins, a solution of (R)-2-methyl-N-(pentan-3-ylidene)propane-2-sulfinamide (3 g, 15.85 mmol) in anhydrous THF (5 mL) was then added dropwise and the mixture was stirred at −78° C. for 5 h. After finished, the mixture was quenched with ice-cold half-saturated aqueous ammonium chloride solution (16 mL). The slurry was diluted with ethyl acetate (30 mL) then filtered, rinsing with ethyl acetate and water. The organic layer was washed with brine (20 mL), dried over Na$_2$SO$_4$, filtered and concentrated in vacuo. The residue was purified by flash column chromatography (SiO$_2$, PE:ethyl acetate=100:0 to 4:1) to afford (R)-methyl 3-(1,1-dimethylethylsulfinamido)-3-ethylpentanoate. HNMR (400 MHz, CDCl₃): δ 4.58 (s, 1H), 3.68 (s, 3H), 2.67-2.71 (m, 1H), 2.49-2.53 (m, 1H), 1.66-1.88 (m, 4H), 1.24 (s, 9H), 0.91 (t, J=7.6 Hz, 3H), 0.86 (t, J=7.6 Hz, 3H). MS (ESI) m/z 264 [M+H]⁺.

Step 3: methyl 3-amino-3-ethylpentanoate hydrochloride

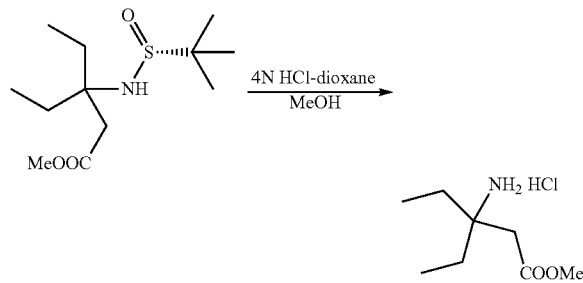

4N HCl-dioxane (7.5 mL) dropwise was added to a solution of (R)-methyl 3-(1,1-dimethylethylsulfinamido)-3-ethylpentanoate (1.5 g, 5.69 mmol) in MeOH (15 mL) at 0° C. The reaction was stirred at 25° C. for 1.5 h. The mixture was azeotropic concentrated with toluene to afford methyl 3-amino-3-ethylpentanoate hydrochloride. HNMR (400 MHz, CDCl₃): δ 8.49 (br s, 2H), 3.75 (s, 3H), 2.81 (s, 2H), 1.87-1.94 (m, 4H), 1.06 (s, 6H).

Step 4: methyl 3-cyano-5-fluorobenzoate

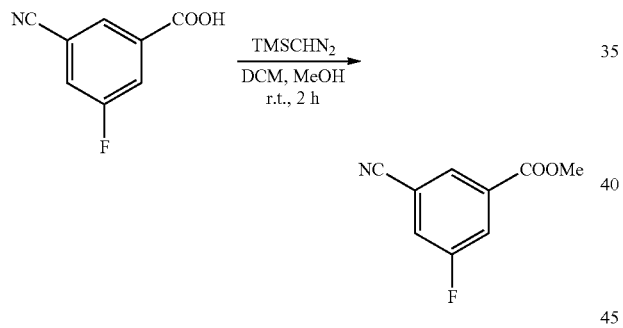

TMS-Diazomethane (30.3 mL, 60.6 mmol) was added to a solution of 3-cyano-5-fluorobenzoic acid (5 g, 30.3 mmol) in DCM (25 mL) and MeOH (25 mL). The mixture was stirred at 25° C. for 2 h. Once finished, the mixture was concentrated in vacuo. The crude was diluted with DCM (30 mL), washed with 1M HCl aq. (15 mL), saturated aqueous NaHCO₃ (15 mL) and brine (30 mL). The organic layer was dried over Na₂SO₄, filtered and concentrated in vacuo to give methyl 3-cyano-5-fluorobenzoate. HNMR (400 MHz, CDCl₃): δ 8.14 (s, 1H), 7.96-7.99 (m, 1H), 7.54-7.57 (m, 1H), 3.98 (s, 3H).

Step 5: methyl 3-(aminomethyl)-5-fluorobenzoate

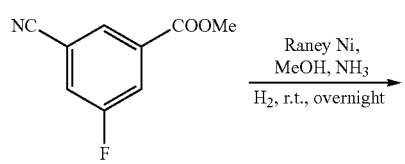

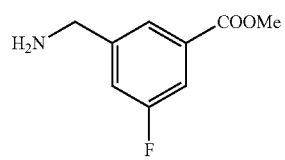

Raney Ni (0.5 g, 27.9 mmol) and NH₃-MeOH (50 mL) were added to a solution of methyl 3-cyano-5-fluorobenzoate (5 g, 27.9 mmol) in MeOH (300 mL). The mixture was stirred at 25° C. for 16 h under H₂ (50 psi) atmosphere. Once finished, the mixture was filtered through a pad of CELITE and the filtrate was concentrated in vacuo. The crude was purified by flash column chromatography (SiO₂, PE:EA=10:1 to EA) to give methyl 3-(aminomethyl)-5-fluorobenzoate. HNMR (400 MHz, CDCl₃): δ 7.79 (s, 1H), 7.57-7.60 (m, 1H), 7.25-7.27 (m, 1H), 3.93 (s, 2H), 3.91 (s, 3H). MS (ESI) m/z 184 [M+H]⁺.

Step 6: methyl 3-((3-(tert-butoxycarbonyl)thioureido)methyl)-5-fluorobenzoate

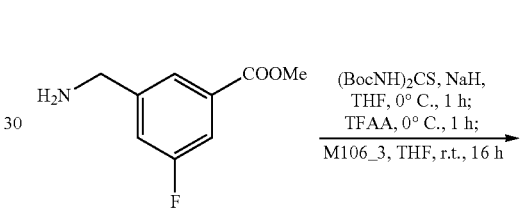

Sodium hydride (0.579 g, 14.47 mmol) was added to a solution of N, N-bisboc-thiourea (2.0 g, 7.24 mmol) in THF (20 mL) was added at 0° C. in portions. After 1 hr at this temperature TFAA (2.012 mL, 14.47 mmol) was added dropwise. The mixture was stirred at 0° C. for 1 h. Then the solution of methyl 3-(aminomethyl)-5-fluorobenzoate (1.989 g, 10.86 mmol) in THF (5 mL) was added dropwise at 0° C. The mixture was stirred at 25° C. for 16 h. The mixture was quenched with water (20 mL), and extracted with ethyl acetate (30 mL×3). The organic layers were washed with brine (20 mL), dried over NaSO₄, filtered, and concentrated in vacuo. The crude was purified by flash column chromatography (SiO₂, PE:EA=100:0 to 10:1) to afford methyl 3-((3-(tert-butoxycarbonyl)thioureido)methyl)-5-fluorobenzoate. HNMR (400 MHz, CDCl₃): 10.10 (s, 1H), 7.99 (s, 1H), 7.81 (s, 1H), 7.65 (d, J=8.8 Hz, 1H), 7.30 (d, J=8.0 Hz, 1H), 4.92 (d, J=6.0 Hz, 2H), 3.94 (s, 3H), 1.49 (s, 9H). MS (ESI) m/z 343 [M+H]⁺.

Step 7: methyl 3-((2-((tert-butoxycarbonyl)imino)-4,4-diethyl-6-oxotetrahydropyrimidin-1 (2H)-yl)methyl)-5-fluorobenzoate

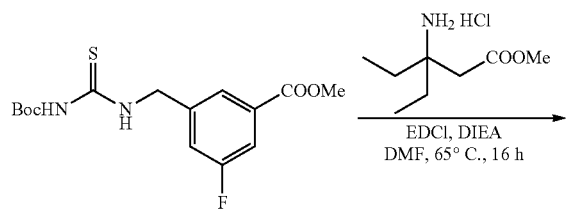

DIEA (2.394 mL, 13.70 mmol), 1-ethyl-3-(3-dimethylaminopropyl)carbodiimide (1051 mg, 5.48 mmol) and methyl 3-amino-3-ethylpentanoate hydrochloride (349 mg, 1.782 mmol) were added to a solution of methyl 3-((3-(tert-butoxycarbonyl)thioureido)methyl)-5-fluorobenzoate (450 mg, 1.370 mmol) in DMF (6 mL). The reaction was heated at 65° C. for 16 h. Once finished, the mixture was quenched with water (20 mL), and extracted with ethyl acetate (20 mL×3). The organic layers were washed with brine (20 mL), dried over Na₂SO₄, filtered, and concentrated in vacuo. The crude was purified by flash column chromatography (SiO₂, PE:EA=100:0 to 5:1) to afford methyl 3-((2-((tert-butoxycarbonyl)imino)-4,4-diethyl-6-oxotetrahydropyrimidin-1 (2H)-yl)methyl)-5-fluorobenzoate. MS (ESI) m/z 436 [M+H]⁺.

Step 8: 3-((2-((tert-butoxycarbonyl)imino)-4,4-diethyl-6-oxotetrahydropyrimidin-1(2H)-yl)methyl)-5-fluorobenzoic acid

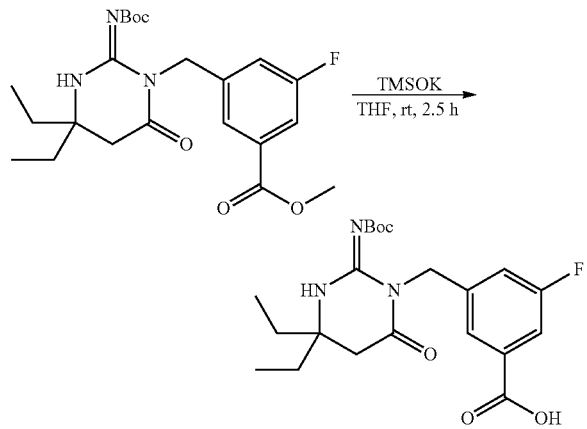

Potassium trimethylsilanolate (147 mg, 1.148 mmol) was added to a solution of methyl 3-((2-((tert-butoxycarbonyl)imino)-4,4-diethyl-6-oxotetrahydropyrimidin-1(2H)-yl)methyl)-5-fluorobenzoate (250 mg, 0.574 mmol) in THF (20 mL). The reaction was stirred at 15° C. for 2.5 h. Once finished, the mixture was concentrated in vacuo. Then water (10 mL) was added to the residue and acidified to pH 5~6 by aqueous 1M HCl, extracted with ethyl acetate (10 mL×3), dried over Na₂SO₄ and concentrated in vacuo to afford 3-((2-((tert-butoxycarbonyl)imino)-4,4-diethyl-6-oxotetrahydropyrimidin-1(2H)-yl)methyl)-5-fluorobenzoic acid. HNMR (400 MHz, MeOD): δ 7.84 (s, 1H), 7.53-7.60 (d, J=8.0 Hz, 1H), 7.35 (d, J=9.2 Hz, 1H), 5.14 (s, 2H), 2.76 (s, 2H), 1.59-1.66 (m, 4H), 1.47 (s, 9H), 0.90 (t, J=7.6 Hz, 6H). MS (ESI) m/z 422 [M+H]⁺.

Step 9: (S)-tert-butyl (4,4-diethyl-1-(3-fluoro-5-(methyl(1-phenylethyl)carbamoyl)benzyl)-6-oxotetrahydropyrimidin-2(1H)-ylidene)carbamate DIEA (0.083 mL, 0.475 mmol) was added to a solution of EDCI (54.6 mg, 0.285 mmol), 3-((2-((tert-butoxycarbonyl)imino)-4,4-diethyl-6-oxotetrahydropyrimidin-1(2H)-yl)methyl)-5-fluorobenzoic acid (40 mg, 0.095 mmol), HOBT (25.6 mg, 0.190 mmol) and (S)—N-methyl-1-phenylethanamine (19.25 mg, 0.142 mmol) in THF (6 mL). The reaction was stirred at 15° C. for 16 h. The mixture was quenched with water (10 mL), and extracted with ethyl acetate (10 mL×3). The organic layers were washed with brine (20 mL), dried over Na₂SO₄, filtered, and concentrated in vacuo to afford (S)-tert-butyl (4,4-diethyl-1-(3-fluoro-5-(methyl(1-phenylethyl)carbamoyl)benzyl)-6-oxotetrahydropyrimidin-2(1H)-ylidene)carbamate. MS (ESI) m/z 539 [M+H]⁺.

Step 10: (S)-3-((4,4-diethyl-2-imino-6-oxotetrahydropyrimidin-1(2H)-yl)methyl)-5-fluoro-N-methyl-N-(1-phenylethyl)benzamide

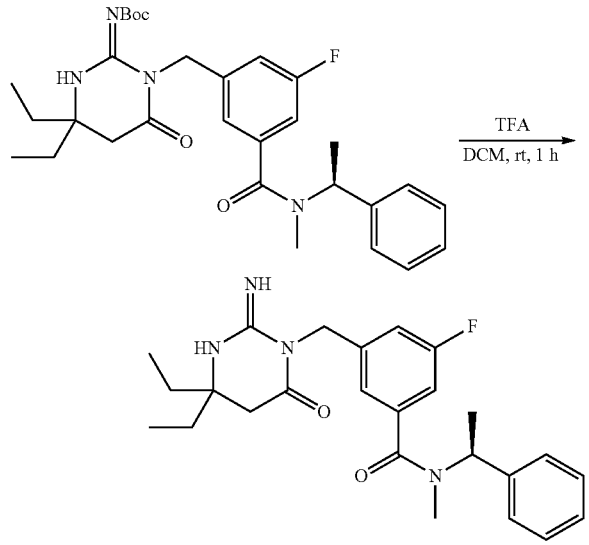

A solution of (S)-tert-butyl (4,4-diethyl-1-(3-fluoro-5-(methyl(1-phenylethyl)carbamoyl)benzyl)-6-oxotetrahydropyrimidin-2(1H)-ylidene)carbamate (50 mg, 0.093 mmol) in DCM (2 mL) and TFA (0.5 mL) was stirred at 15° C. for 1 h. The mixture was concentrated in vacuo and the crude was purified by Prep-HPLC (0.1% TFA) to afford (S)-3-((4,4-diethyl-2-imino-6-oxotetrahydropyrimidin-1(2H)-yl)methyl)-5-fluoro-N-methyl-N-(1-phenylethyl)benzamide (25 mg, 0.057 mmol). HNMR (400 MHz, $CDCl_3$): δ 10.84 (br s, 1H), 7.28-7.42 (m, 4H), 7.17 (s, 2H), 7.03 (s, 2H), 5.16 (s, 2H), 4.95 (brs, 1H), 3.20 (s, 3H), 2.78 (s, 2H), 1.55-1.69 (m, 7H), 0.89 (s, 6H). MS (ESI) m/z 439 $[M+H]^+$ Biological Assays Assay 1

Summary:

A modified version of the assay described in Gamo, F. J., Sanz, L. M., Vidal, J., de Cozar, C., Alvarez, E., Lavandera, J. L., Vanderwall, D. E., Green, D. V., Kumar, V., Hasan, S., Brown, J. R., Peishoff, C. E., Cardon, L. R., Garcia-Bustos, J. F., Nature, 465 (2010) 305-310 (Gamo et al.) was used to assess the activity of compounds against asexual P. falciparum 3D7 parasites. Compounds were pre-dispensed in 384-well plates, RPMI/AlbuMAX growth media was added and P. falciparum inoculated. Plates were incubated for 72 h and then frozen at −80° C. overnight. Lactate dehydrogenase (LDH) activity was quantified with the modified cofactor 3-acetylpyridine adenine dinucleotide (APAD) (Sigma Aldrich) by measuring absorbance of the tetrazolium indicator nitro blue tetrazolium (NBT) (Sigma Aldrich) at 650 nm.

Parasite Conditions:

An inoculum of synchronous P. falciparum (3D7 strain) parasitized red blood cells (PRBC) at 0.7% parasitaemia and 2% haematocrit in RPMI-1640, 5% AlbuMAX, 2% D-sucrose, 0.3% glutamine and 150 μM hypoxanthine was used for the assay.

Growth Inhibition Assay:

Compound master plates (384-well) were prepared by a 10 pt serial dilution of compounds, from 1 mM to 50.8 nM, in columns 3-12 and 13-22. DMSO was dispensed into columns 1 and 23 of the compound master plate to be used as the positive growth control (100% viability). Columns 2 and 24 of the compound master plate had a stock concentration of 200 μM chloroquine solution (0% viability) as negative growth control (final assay concentration of 200 nM). Intermediate compound dilution plates were prepared by dispensing 1 μl from each well of the compound master plate into 11.5 μl of RPMI/AlbuMAX growth media. Duplicate assay plates (384-well) were then prepared by dispensing 0.5 μL of compound from the intermediate dilution plates into 9.5 μl of RPMI/AlbuMAX growth media. The parasite inoculum (30 μL) was dispensed into the assay plates containing compounds using a Multidrop dispenser (Thermo Scientific) such that the final assay volume was 40 μL and final compound concentration was 1 μM-0.05 nM (the volume of compound addition can be adjusted to the preferred and agreed screening concentration). The final DMSO concentration was 0.1% (ideally 0.2% to limit toxicity to parasites), but this is dependent on volume of compound DMSO stock solution that can be supplied. Plates were incubated at 37° C. for 72 h in an atmosphere of 5% $CO_2$, 5% $O_2$, 95% $N_2$.

Evaluation of Parasite Growth Measuring LDH Activity:

After 72 h of incubation, plates were frozen at −80° C. overnight and then thawed at room temperature for at least 4 h. To evaluate LDH activity, 45 μL of freshly made reaction mix (174 mM sodium L-lactate (Sigma Aldrich), 214 μM 3-acetyl pyridine adenine dinucleotide (APAD) (Sigma Aldrich), 270 μM nitro blue tetrazolium chloride (NBT) (Sigma Aldrich), 4.35 U/mL diaphorase (from Clostridium kluyveri) (Sigma Aldrich), 0.7% Tween 20, 100 mM Tris-HCl pH 7.5) was dispensed using a Multidrop dispenser (Thermo Scientific). Plates were shaken to ensure mixing and absorbance at 650 nm was monitored using a Perkin Elmer Envision plate reader after 30 min of incubation at room temperature. Data were normalized to percent growth inhibition using positive and negative controls, and analysed using TIBCO Spotfire software.

Counterscreen:

A buffered solution of 30 μL Bovine LDH (12.5 U/ml) (Sigma Aldrich) was dispensed into compound ready plates. The same protocol then was undertaken for measuring the LDH activity using parasites.

Assay 2

The assay described in Gamo et al. is as follows:

P. falciparum strains 3D7 and Dd2 used in this study were obtained from the Malaria Research and Reference Reagent Resource Center (MR4). Parasite strains were cultured using standard procedures as described (Trager, W. & Jensen, J. B. Science 193, 673-675 (1976)). An inoculum of parasitized red blood cells (PRBC) at 0.25% parasitaemia and 2% haematocrit in RPMI-1640, 5% AlbuMAX, 2% D-sucrose, 0.3% glutamine and 150 μM hypoxanthine was used for the assay.

Assay plates were prepared by dispensing 0.05 μl of compound from master plates at 1 mM in each well. Final assay volume was 25 μl and final compound concentration was 2 μM. The sixth column was the positive growth control and had 0.05 μl of DMSO. The eighteenth column had 0.05 μl of a mixture of 50 μM chloroquine and 50 μM artemisinin stock solutions as using a negative growth control. The parasite inoculum (25 μl) was dispensed into plates containing compounds Multidrop Combi dispenser (Thermo Scientific). Plates were shaken for 10 s to ensure mixing and then incubated at 37° C. for 72 hours in an atmosphere of 5% $CO_2$, 5% $O_2$, 95% $N_2$.

Evaluation of Parasite Growth Using Lactate Dehydrogenase (LDH) Activity

After 72 hours of incubation, plates were frozen at −70° C. overnight and then thawed at room temperature for at least 4 hours. To evaluate LDH activity, 70 µl of freshly made reaction mix (143 mM sodium 1-lactate, 143 µM 3-acetyl pyridine adenine dinucleotide (APAD), 178.75 µM Nitro Blue tetrazolium chloride (NBT), 286 µg ml$^{-1}$ diaphorase (2.83 U ml$^{-1}$), 0.7% Tween 20, 100 mM Tris-HCl pH 8.0) was dispensed using a Multidrop Combi dispenser. Plates were shaken to ensure mixing, and absorbance at 650 nm was monitored in a plate reader after 10 min of incubation at room temperature. Data were normalized to percent growth inhibition using positive and negative controls and the equation:

$$\text{Percentage inhibition growth} = \left[1 - \left(\frac{A_{well} - A_{neg}}{A_{pos} - A_{neg}}\right)\right] \times 100$$

where $A_{well}$ is the absorbance measured in the well, and $A_{pos}$ and $A_{neg}$ are the average absorbances measured for the positive and negative controls, respectively. This method is a modification of existing ones (Makler et al., Measurement of the lactate dehydrogenase activity of *Plasmodium falciparum* as an assessment of parasitemia. Am. J. Trop. Med. Hyg. 48: 205-210 (1993)) that requires only a single pipetting step after compound incubation and gave a signal to noise ratio of 10 under the conditions chosen. The approach allowed kinetic and end-point readouts and produced a Z' quality factor (Zhang et al., J. Biomol. Screen. 4: 67-73 (1999)) higher than 0.7 in validation assays (Supplementary FIG. 2, Gamo et al., Nature 465:305-312 (2010)). Potencies of standard antimalarial agents in this assay were comparable to those determined by the current gold-standard, 96-well, hypoxanthine incorporation assay (Desjardins et al. Quantitative assessment of antimalarial activity in vitro by a semiautomated microdilution technique. Antimicrob. Agents Chemother. 16: 710-718 (1979)) (Supplementary Table 3, Gamo et al., 2010, supra).

At this level of miniaturization, integrity of erythrocytes and LDH activity can be inspected visually, allowing for rapid detection of dispensing errors, interference by colored compounds, or haemolysis, making the method very useful for low technology settings (Supplementary FIG. 3, Gamo et al., 2010, supra). Proliferation of asynchronous parasites was measured after 72 h of incubation in the presence of 2 µM compound. We chose a 72 hour incubation time to ensure all parasites traversed at least once through each stage of the cell cycle and to increase the chances of identifying slow acting and 'delayed death phenotype' inhibitors (Goodman et al., The effects of anti-bacterials on the malaria parasite *Plasmodium falciparum*. Mol. Biochem. Parasitol. 152, 181-191 (2007); Ramya et al., A. Inhibitors of nonhousekeeping functions of the apicoplast defy delayed death in *Plasmodium falciparum*. Antimicrob. Agents Chemother. 51, 307-316 (2007)).

Given the large number of positives, it was necessary to estimate the concentrations producing 50% inhibition using the LDH assay above and generating dose-response curves with fivefold dilution steps down to 3 nM compound in an interplate design, instead of using the hypoxanthine incorporation assay with two-fold dilution intraplate series generally considered the standard method to calculate IC$_{50}$ for antimalarials (Fidock et al., Antimalarial drug discovery: Efficacy models for compound screening. Nature Rev. Drug Discov. 3, 509-520 (2004)). The lowest concentration tested was 3 nM. Agreement between the two methods was found to be within the expected limits with standard antimalarials (Supplementary Table 3, Gamo et al., 2010, supra). To eliminate the possibility of retaining inhibitors of the biochemical readout system, one set of the primary hits was assayed against parasite LDH activity under identical screening conditions.

Preparation of Extracts to Evaluate Direct LDH Inhibition by Hit Compounds

*P. falciparum* 3D7 strain was grown as described in Assay 1, at 37° C. for 72 hours. The culture was frozen at −80° C. overnight. Cultures were thawed at room temperature for at least 4 hours and the reaction mixture described in Assay 1 was made in order to measure the possible direct inhibition of LDH by the following compounds, assayed as above in Assay 1.

| Compound No. | Structure | *P. falciparum* LDH IC$_{50}$ Value (µM) |
|---|---|---|
| 1 | 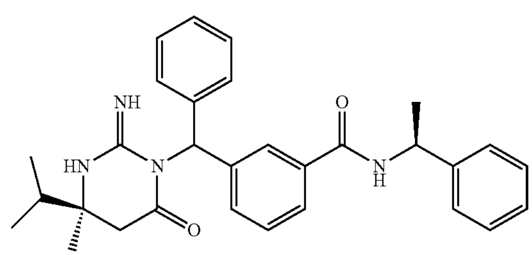 [SMILES: CC(C)[C@]1(C)CC(=O)N(C(c2ccccc2)c2cccc(C(=O)N[C@@H](C)c3ccccc3)c2)C(=N)N1] | 0.003 |

-continued

| Compound No. | Structure | P. falciparum LDH IC$_{50}$ Value (μM) |
|---|---|---|
| 2 | Chiral | 0.00130 |
| 3 | Chiral | 0.00137 |
| 4 | 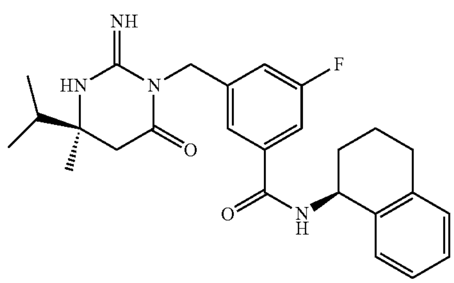 [SMILES: CC(C)[C@]1(C)CC(=O)N(Cc2cc(F)cc(C(=O)N[C@H]3CCCc4ccccc43)c2)C(=N)N1] | 0.00168 |
| 5 | Chiral | 0.00253 |

-continued
| Compound No. | Structure | P. falciparum LDH IC$_{50}$ Value (μM) |
|---|---|---|
| 6 | 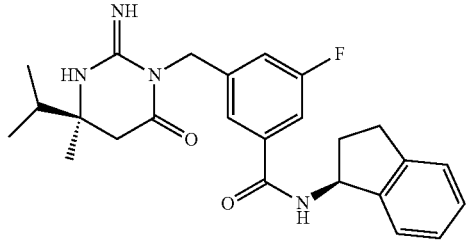 [SMILES: CC(C)[C@]1(C)CC(=O)N(Cc2cc(F)cc(C(=O)N[C@H]3CCc4ccccc43)c2)C(=N)N1] | 0.00292 |
| 7 | 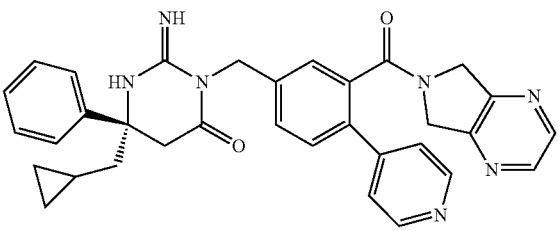 Chiral | 0.00327 |
| 8 | 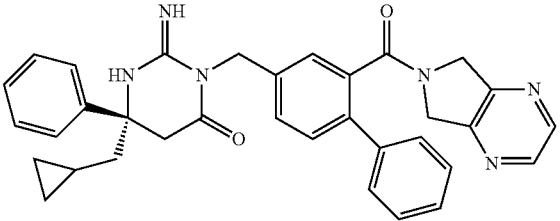 [SMILES: N=C1N[C@](CC2CC2)(c2ccccc2)CC(=O)N1Cc1ccc(-c2ccccc2)c(C(=O)N2Cc3nccnc3C2)c1] Chiral | 0.00342 |
| 9 | 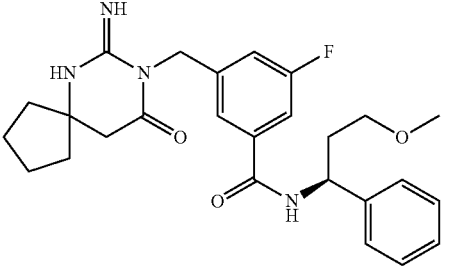 [SMILES: COCC[C@H](NC(=O)c1cc(F)cc(CN2C(=N)NC3(CCCC3)CC2=O)c1)c1ccccc1] Chiral | 0.00419 |
| 10 | 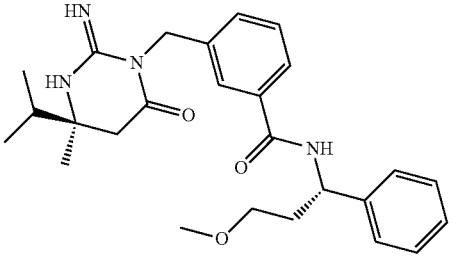 [SMILES: COCC[C@H](NC(=O)c1cccc(CN2C(=N)N[C@](C)(C(C)C)CC2=O)c1)c1ccccc1] Chiral | 0.00534 |

-continued
| Compound No. | Structure | P. falciparum LDH IC$_{50}$ Value (μM) |
|---|---|---|
| 11 | 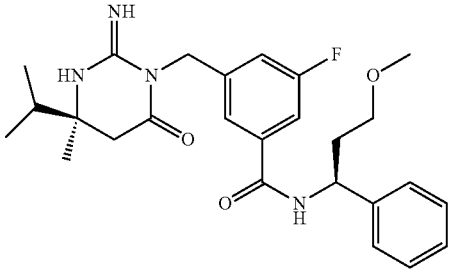 [SMILES: COCC[C@H](NC(=O)c1cc(F)cc(CN2C(=N)N[C@](C)(C(C)C)CC2=O)c1)c1ccccc1]<br>Chiral | 0.00567 |
| 12 | 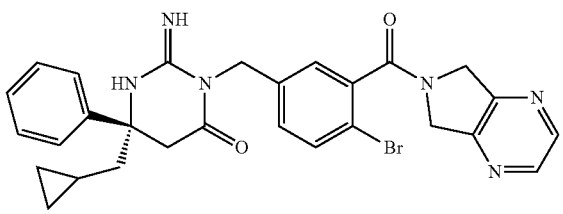 [SMILES: N=C1N[C@](CC2CC2)(c2ccccc2)CC(=O)N1Cc1ccc(Br)c(C(=O)N2Cc3nccnc3C2)c1]<br>Chiral | 0.00601 |
| 13 | 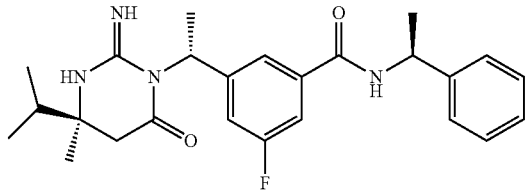 [SMILES: CC(C)[C@]1(C)CC(=O)N([C@H](C)c2cc(F)cc(C(=O)N[C@@H](C)c3ccccc3)c2)C(=N)N1] | 0.00643 |
| 14 | 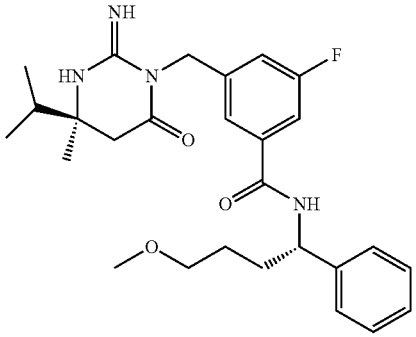 [SMILES: COCCC[C@H](NC(=O)c1cc(F)cc(CN2C(=N)N[C@](C)(C(C)C)CC2=O)c1)c1ccccc1]<br>Chiral | 0.00662 |
| 15 | 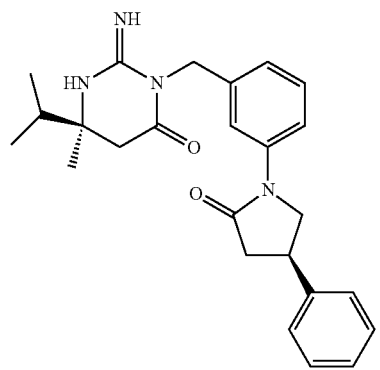 [SMILES: CC(C)[C@]1(C)CC(=O)N(Cc2cccc(N3C[C@@H](c4ccccc4)CC3=O)c2)C(=N)N1]<br>Chiral | 0.00774 |

-continued

| Compound No. | Structure | *P. falciparum* LDH IC$_{50}$ Value (μM) |
|---|---|---|
| 16 | Chiral | 0.00806 |
| 17 | Chiral | 0.01056 |
| 18 | 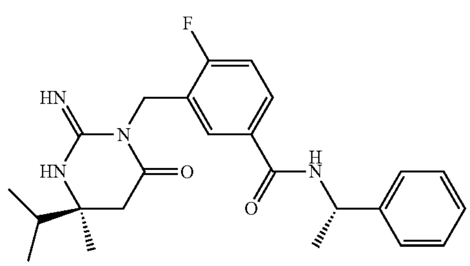 [SMILES: CC(C)[C@]1(C)CC(=O)N(Cc2cc(C(=O)N[C@@H](C)c3ccccc3)ccc2F)C(=N)N1] | 0.0129 |
| 19 | Chiral | 0.0140 |

-continued

| Compound No. | Structure | *P. falciparum* LDH IC$_{50}$ Value (μM) |
|---|---|---|
| 20 | Chiral | 0.0140 |
| 21 | 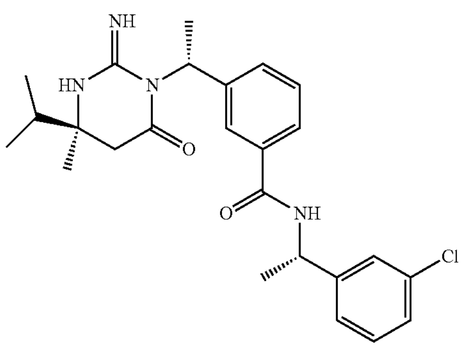 [SMILES: CC(C)[C@]1(C)CC(=O)N([C@H](C)c2cccc(C(=O)N[C@@H](C)c3cccc(Cl)c3)c2)C(=N)N1] | 0.0199 |
| 22 | Chiral | 0.0272 |
| 23 | Chiral | 0.0330 |

-continued

| Compound No. | Structure | *P. falciparum* LDH IC$_{50}$ Value (μM) |
|---|---|---|
| 24 | 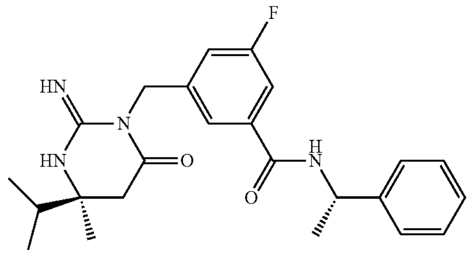 [SMILES: CC(C)[C@]1(C)CC(=O)N(Cc2cc(F)cc(C(=O)N[C@@H](C)c3ccccc3)c2)C(=N)N1] | 0.0488 |
| 25 | Chiral | 0.1390 |
| 26 | Chiral | 0.3710 |
| 27 | First eluting diasteriomer | 0.014 |

| Compound No. | Structure | *P. falciparum* LDH IC$_{50}$ Value (μM) |
|---|---|---|
| 28 | 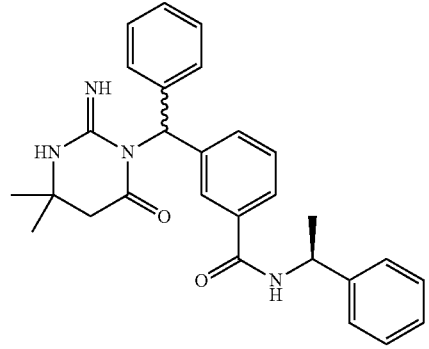 [SMILES: C[C@H](NC(=O)c1cccc(C(c2ccccc2)N2C(=N)NC(C)(C)CC2=O)c1)c1ccccc1] Second eluting diasteriomer | >1.000 |
| 29 | 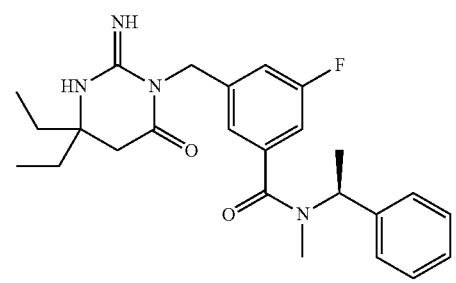 [SMILES: CCC1(CC)CC(=O)N(Cc2cc(F)cc(C(=O)N(C)[C@@H](C)c3ccccc3)c2)C(=N)N1] | 0.870 |
| 30 | 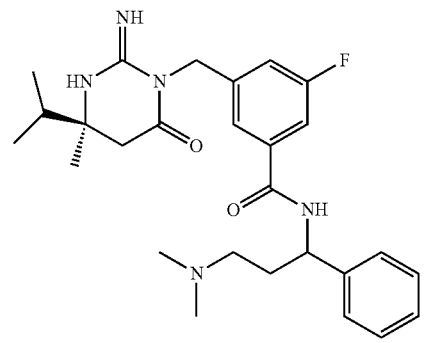 [SMILES: CC(C)[C@]1(C)CC(=O)N(Cc2cc(F)cc(C(=O)NC(CCN(C)C)c3ccccc3)c2)C(=N)N1] | 0.260 |
| 31 | 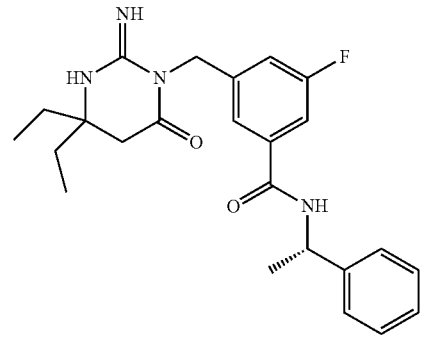 [SMILES: CCC1(CC)CC(=O)N(Cc2cc(F)cc(C(=O)N[C@@H](C)c3ccccc3)c2)C(=N)N1] | 0.094 |

-continued

| Compound No. | Structure | *P. falciparum* LDH IC$_{50}$ Value (μM) |
|---|---|---|
| 32 | 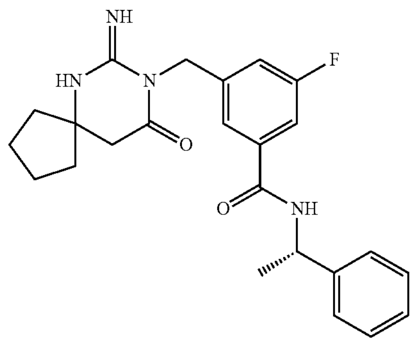 [SMILES: C[C@H](NC(=O)c1cc(F)cc(CN2C(=N)NC3(CCCC3)CC2=O)c1)c1ccccc1] | 0.500 |
| 33 | 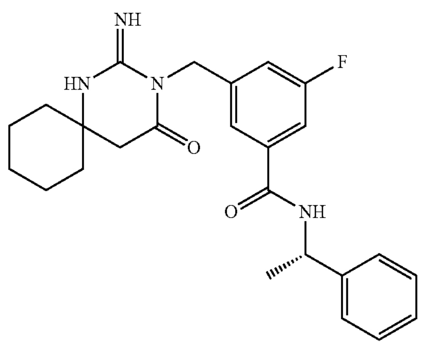 [SMILES: C[C@H](NC(=O)c1cc(F)cc(CN2C(=N)NC3(CCCCC3)CC2=O)c1)c1ccccc1] | 0.260 |
| 34 | 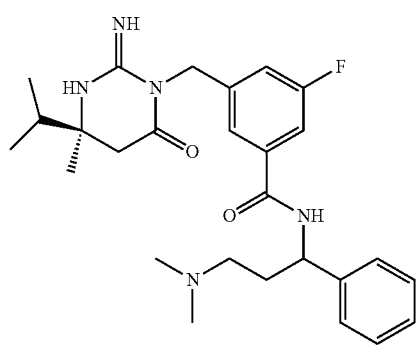 [SMILES: CC(C)[C@]1(C)CC(=O)N(Cc2cc(F)cc(C(=O)NC(CCN(C)C)c3ccccc3)c2)C(=N)N1] | 0.310 |
| 35 | 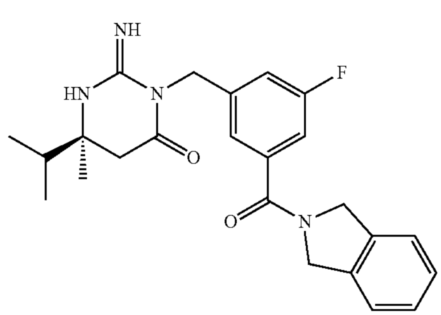 [SMILES: CC(C)[C@]1(C)CC(=O)N(Cc2cc(F)cc(C(=O)N3Cc4ccccc4C3)c2)C(=N)N1] | 0.390 |

-continued

| Compound No. | Structure | *P. falciparum* LDH IC$_{50}$ Value (μM) |
|---|---|---|
| 36 | 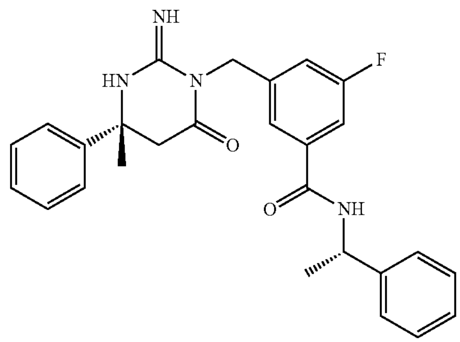 [SMILES: C[C@H](NC(=O)c1cc(F)cc(CN2C(=N)N[C@@](C)(c3ccccc3)CC2=O)c1)c1ccccc1] | 0.130 |
| 37 | 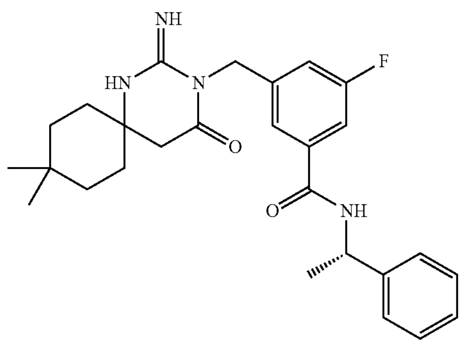 [SMILES: C[C@H](NC(=O)c1cc(F)cc(CN2C(=N)NC3(CCC(C)(C)CC3)CC2=O)c1)c1ccccc1] | 0.620 |
| 38 | 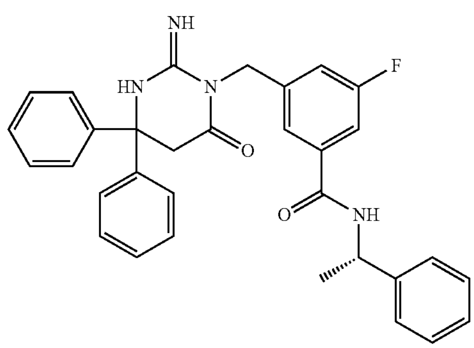 [SMILES: C[C@H](NC(=O)c1cc(F)cc(CN2C(=N)NC(c3ccccc3)(c3ccccc3)CC2=O)c1)c1ccccc1] | 0.570 |
| 39 | 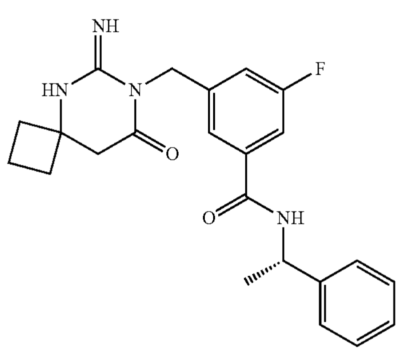 [SMILES: C[C@H](NC(=O)c1cc(F)cc(CN2C(=N)NC3(CCC3)CC2=O)c1)c1ccccc1] | 1.000 |
| 40 | 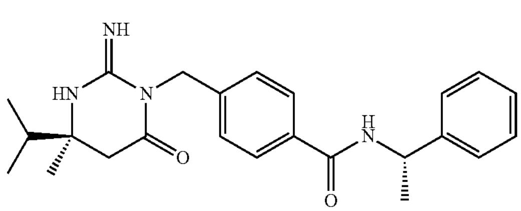 [SMILES: CC(C)[C@]1(C)CC(=O)N(Cc2ccc(C(=O)N[C@@H](C)c3ccccc3)cc2)C(=N)N1] | 0.630 |

-continued

| Compound No. | Structure | P. falciparum LDH IC$_{50}$ Value (μM) |
|---|---|---|
| 41 | 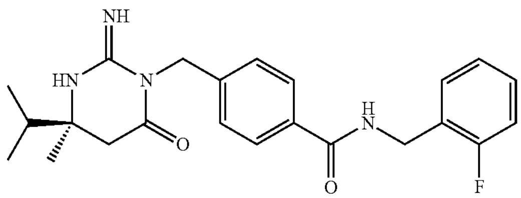 [SMILES: CC(C)[C@]1(C)CC(=O)N(Cc2ccc(C(=O)NCc3ccccc3F)cc2)C(=N)N1] | 0.430 |
| 42 | 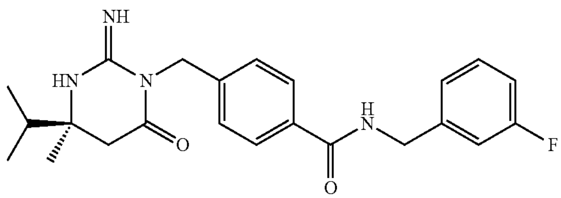 [SMILES: CC(C)[C@]1(C)CC(=O)N(Cc2ccc(C(=O)NCc3cccc(F)c3)cc2)C(=N)N1] | 0.480 |
| 43 | 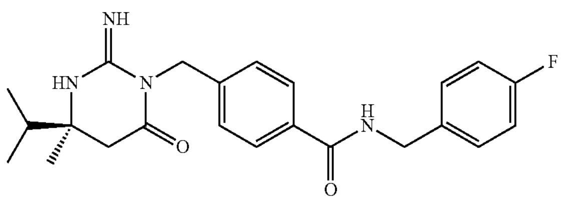 [SMILES: CC(C)[C@]1(C)CC(=O)N(Cc2ccc(C(=O)NCc3ccc(F)cc3)cc2)C(=N)N1] | 0.860 |
| 44 | 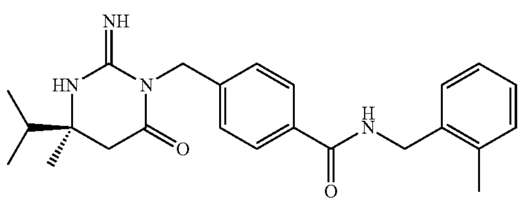 [SMILES: Cc1ccccc1CNC(=O)c1ccc(CN2C(=N)N[C@](C)(C(C)C)CC2=O)cc1] | 0.320 |
| 45 | 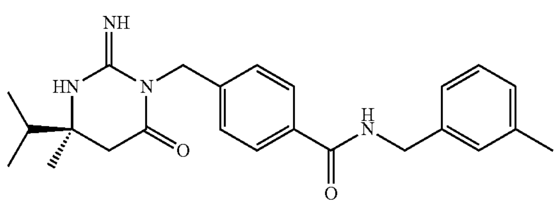 [SMILES: Cc1cccc(CNC(=O)c2ccc(CN3C(=N)N[C@](C)(C(C)C)CC3=O)cc2)c1] | 0.810 |
| 46 | 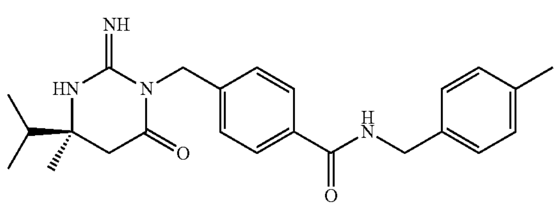 [SMILES: Cc1ccc(CNC(=O)c2ccc(CN3C(=N)N[C@](C)(C(C)C)CC3=O)cc2)cc1] | 0.550 |
| 47 | 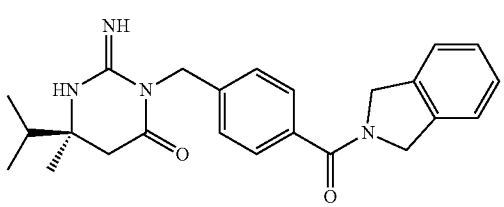 [SMILES: CC(C)[C@]1(C)CC(=O)N(Cc2ccc(C(=O)N3Cc4ccccc4C3)cc2)C(=N)N1] | 0.490 |

-continued

| Compound No. | Structure | *P. falciparum* LDH IC$_{50}$ Value (μM) |
|---|---|---|
| 48 | 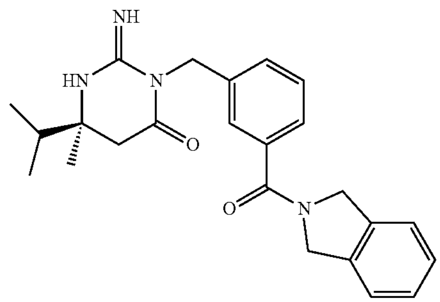 [SMILES: CC(C)[C@]1(C)CC(=O)N(Cc2cccc(C(=O)N3Cc4ccccc4C3)c2)C(=N)N1] | |
| 49 | 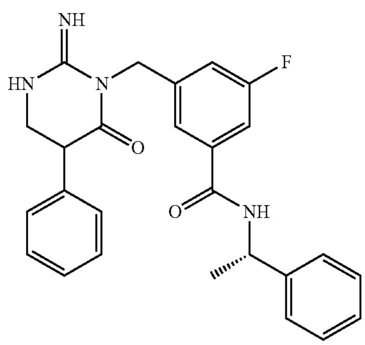 [SMILES: C[C@H](NC(=O)c1cc(F)cc(CN2C(=N)NCC(c3ccccc3)C2=O)c1)c1ccccc1] | 0.770 |
| 50 | 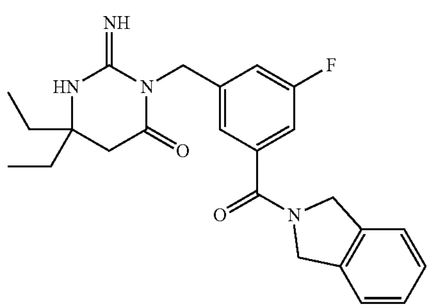 [SMILES: CCC1(CC)CC(=O)N(Cc2cc(F)cc(C(=O)N3Cc4ccccc4C3)c2)C(=N)N1] | 0.610 |
| 51 | 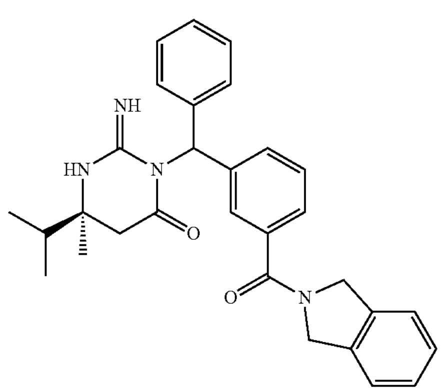 [SMILES: CC(C)[C@]1(C)CC(=O)N(C(c2ccccc2)c2cccc(C(=O)N3Cc4ccccc4C3)c2)C(=N)N1] | 0.049 |

-continued

| Compound No. | Structure | P. falciparum LDH IC$_{50}$ Value (μM) |
|---|---|---|
| 52 | 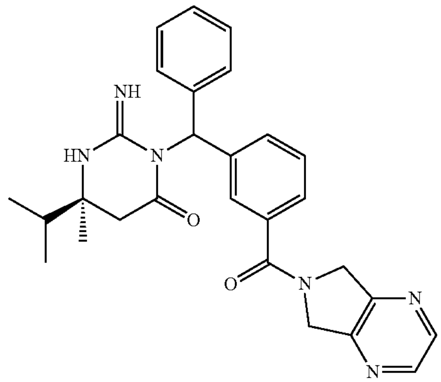 [SMILES: CC(C)[C@]1(C)CC(=O)N(C(c2ccccc2)c2cccc(C(=O)N3Cc4nccnc4C3)c2)C(=N)N1] | 0.270 |
| 53 | 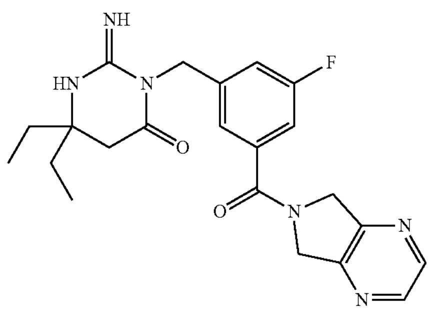 [SMILES: CCC1(CC)CC(=O)N(Cc2cc(F)cc(C(=O)N3Cc4nccnc4C3)c2)C(=N)N1] | 0.870 |
| 54 | 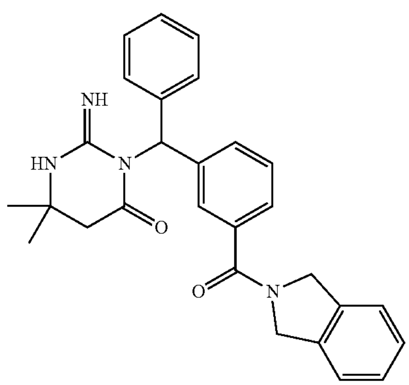 [SMILES: CC1(C)CC(=O)N(C(c2ccccc2)c2cccc(C(=O)N3Cc4ccccc4C3)c2)C(=N)N1] | 0.390 |
| 55 | 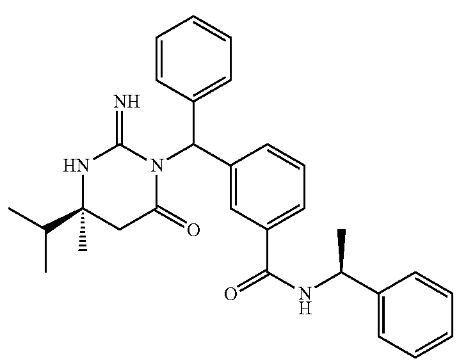 [SMILES: CC(C)[C@]1(C)CC(=O)N(C(c2ccccc2)c2cccc(C(=O)N[C@@H](C)c3ccccc3)c2)C(=N)N1] | 0.0035 |

| Compound No. | Structure | P. falciparum LDH IC$_{50}$ Value (µM) |
|---|---|---|
| 56 | 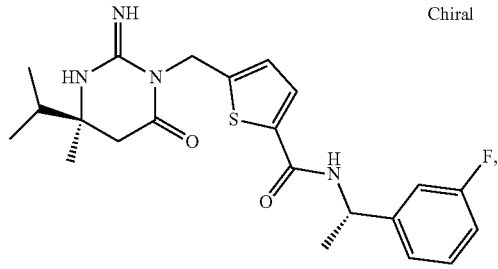 | 0.360 |

What is claimed:

1. A method for treating a *Plasmodium* infection, or for treating malaria, wherein the *Plasmodium* strain is drug resistant, consisting of administering to a subject in need of such treatment a therapeutically effective amount of a compound, and a pharmaceutically acceptable carrier, said compound having the structure:

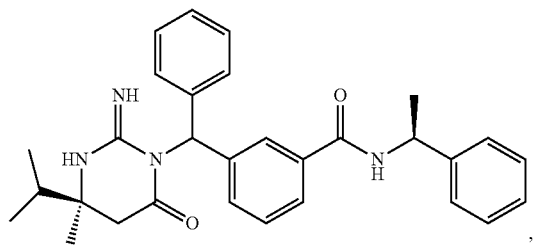

Chiral

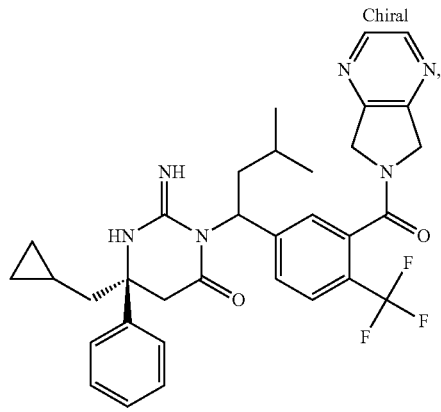

Chiral

-continued

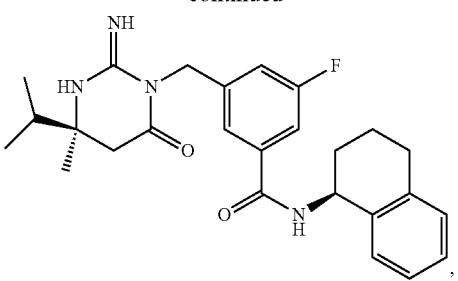

Chiral

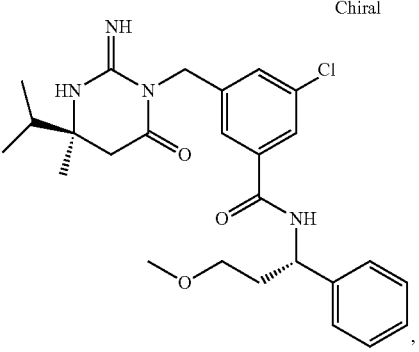

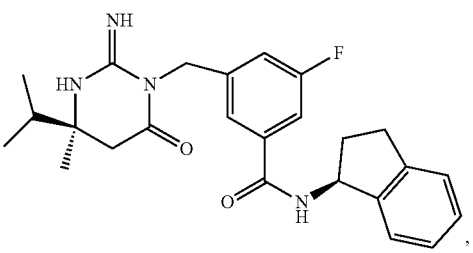

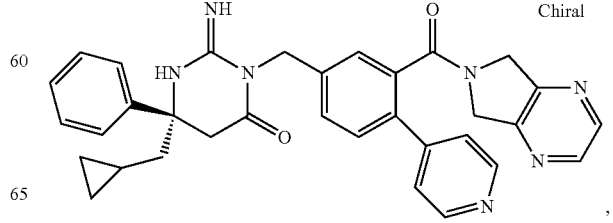

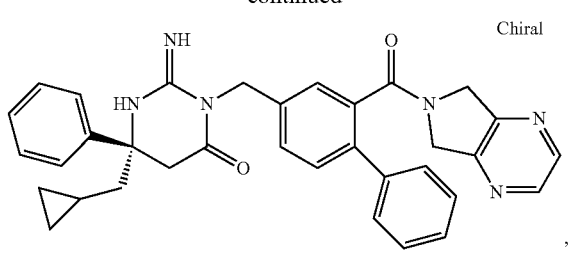
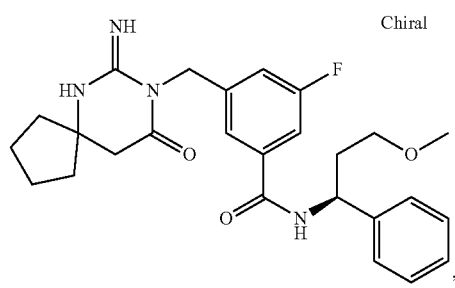
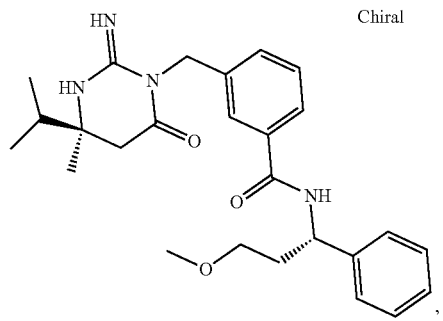
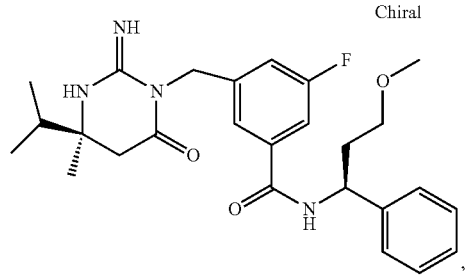
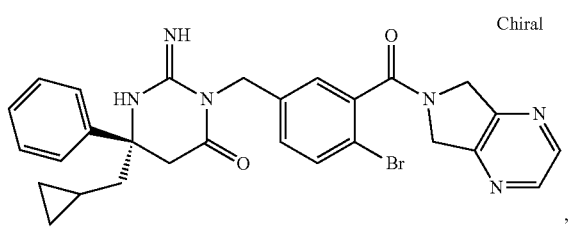
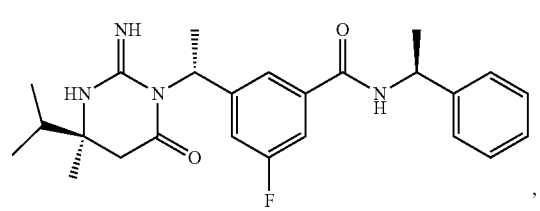
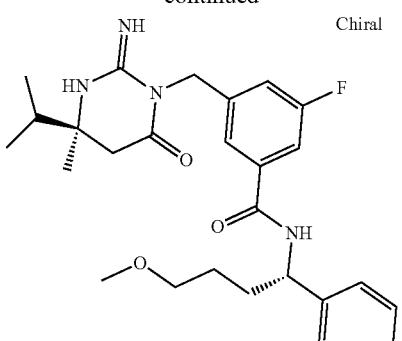
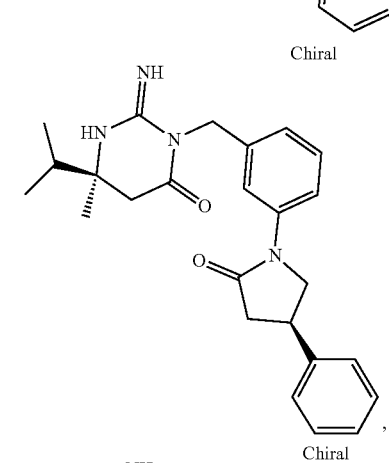
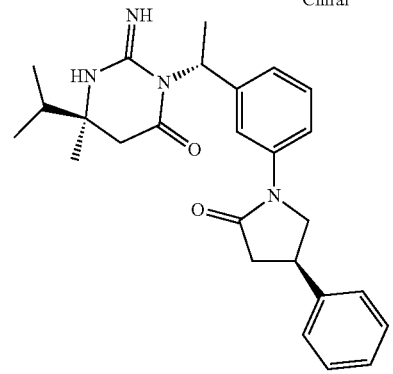
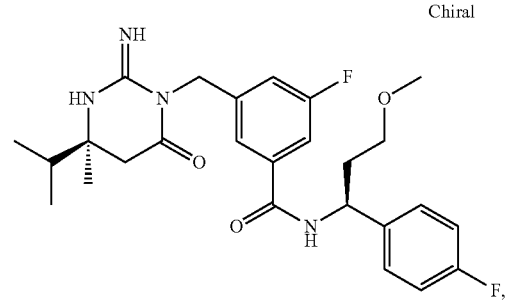
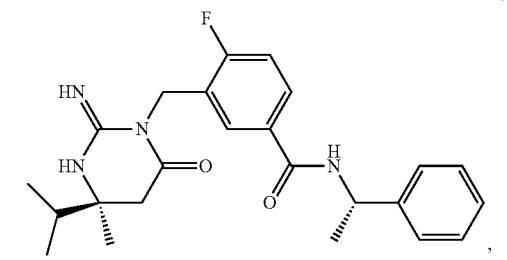

-continued

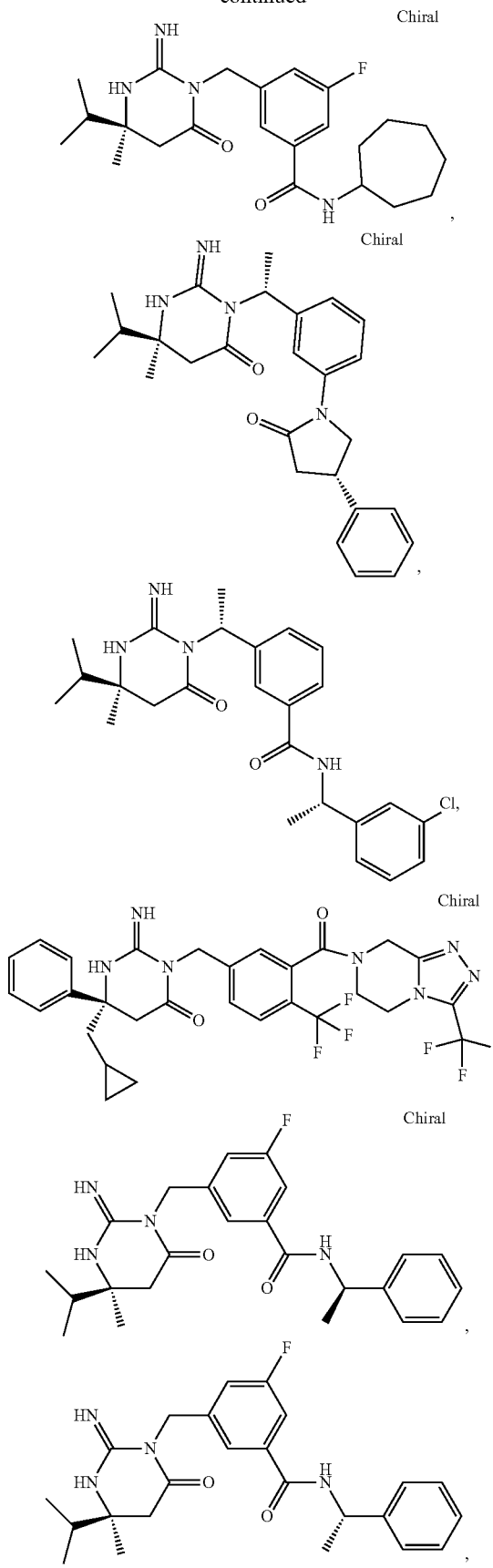

-continued

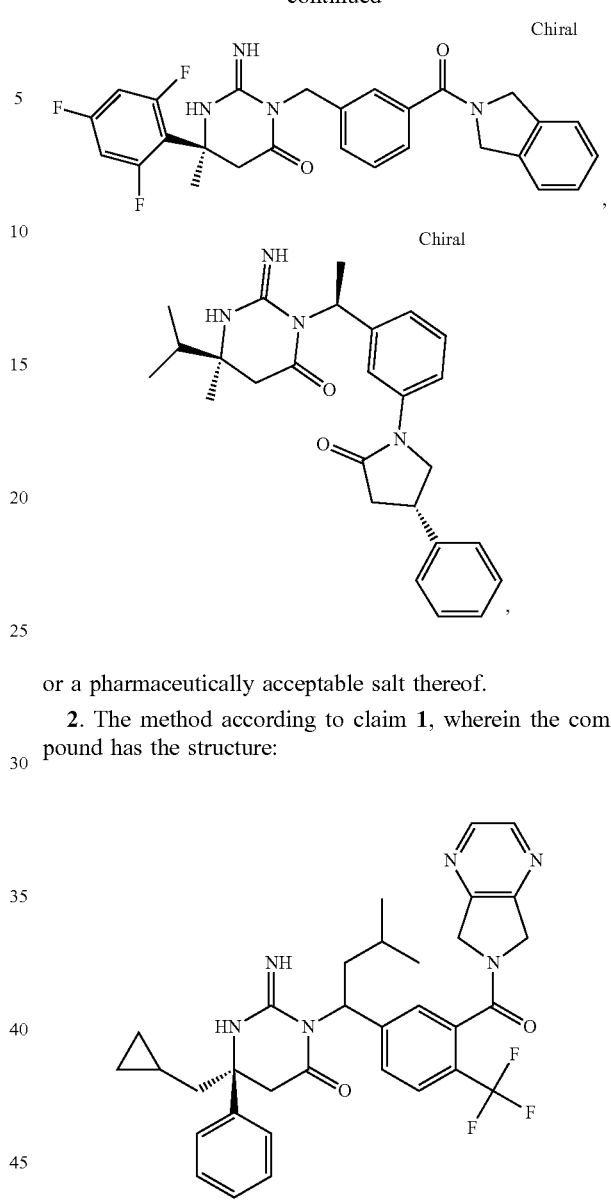

or a pharmaceutically acceptable salt thereof.

2. The method according to claim 1, wherein the compound has the structure:

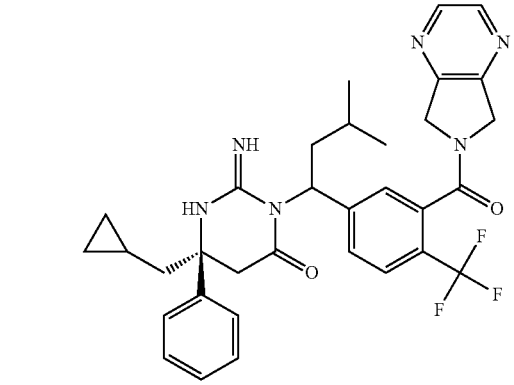 [SMILES: CC(C)CC(c1ccc(C(F)(F)F)c(C(=O)N2Cc3nccnc3C2)c1)N1C(=N)N[C@](CC2CC2)(c2ccccc2)CC1=O]

or a pharmaceutically acceptable salt thereof.

3. The method of claim 1, wherein the subject is human.

4. The method of claim 3, wherein the compound or the pharmaceutically acceptable salt thereof is administered orally or via subcutaneous, intramuscular, or intravenous administration.

5. The method of claim 1, wherein the method further consists of administration of one or more additional anti-malarial treatments to the subject.

6. The method of claim 5, wherein the one or more additional anti-malarial treatment is selected from the group consisting of: artemether, lumefantrine, dihydroartemisinin, piperaquine, pyronaridine, artesunate, amodiaquine, mefloquine, sulfadoxine, pyrimethamine, lumefantrine, quinine, chloroquine, atovaquone, and proguanil.

* * * * *